US011964882B2

United States Patent
Cho et al.

(10) Patent No.: US 11,964,882 B2
(45) Date of Patent: Apr. 23, 2024

(54) IOT-BASED SYSTEM FOR MEASUREMENT OF CONTAMINATION DISTRIBUTION OF CONTAMINATED GROUNDWATER THROUGH REAL-TIME MONITORING OF CONTAMINATION DEGREE OF CONTAMINATED GROUNDWATER WELL FOR CONTROL OF CONTAMINATED GROUNDWATER PURIFICATION DEVICE AND PREDICTION OF PURIFICATION PERIOD BASED ON MEASUREMENT RESULT

(71) Applicant: HYORIM Co., Ltd., Seongnam-si (KR)

(72) Inventors: Sung Kook Cho, Pyeongtaek-si (KR); Seong Ghui Cho, Pohang-si (KR); Myeong Gwang Oh, Yongin-si (KR); Sang Hwan Lee, Gangneung-si (KR)

(73) Assignees: Sung Kook Cho (KR); HYORIM CO., LTD. (KR)

( * ) Notice: Subject to any disclaimer, the term of this patent is extended or adjusted under 35 U.S.C. 154(b) by 1138 days.

(21) Appl. No.: 16/711,785

(22) Filed: Dec. 12, 2019

(65) Prior Publication Data

US 2021/0179446 A1    Jun. 17, 2021

(51) Int. Cl.
*C02F 1/00* (2023.01)
*C02F 103/06* (2006.01)
(Continued)

(52) U.S. Cl.
CPC ......... *C02F 1/008* (2013.01); *G01N 21/3103* (2013.01); *G01N 21/33* (2013.01);
(Continued)

(58) Field of Classification Search
CPC .................. C02F 1/008; C02F 2103/06; C02F 2209/006; C02F 2209/02; C02F 2209/06;
(Continued)

(56) References Cited

U.S. PATENT DOCUMENTS

| 2006/0026535 A1* | 2/2006 | Hotelling ............... G06F 3/0488 715/863 |
| 2011/0278232 A1* | 11/2011 | Al-Jlil ....................... C02F 1/62 210/711 |

(Continued)

FOREIGN PATENT DOCUMENTS

| KR | 10-0978939 B1 | 8/2010 |
| KR | 100978939 B1 * | 8/2010 |

(Continued)

OTHER PUBLICATIONS

Pandey, Piyush Kant, et al. "Arsenic contamination of the environment: a new perspective from central-east India." Environment International 28.4 (2002): 235-245. (Year: 2002).*

(Continued)

*Primary Examiner* — Boris Gorney
*Assistant Examiner* — Pursottam Giri
(74) *Attorney, Agent, or Firm* — Park & Associates IP Law Office

(57) ABSTRACT

An IoT-based system for measurement of contamination distribution of contaminated groundwater through real-time monitoring of a contamination degree of a contaminated groundwater well for control of a contaminated groundwater purification device and prediction of a purification period based on the measurement result. The IoT-based system for measurement of contamination distribution of contaminated groundwater through real-time monitoring of a contamination degree of a contaminated groundwater well for control of a contaminated groundwater purification device and pre- (Continued)

diction of a purification period based on the measurement result monitors a groundwater well in real time based on sensor data collected from the contaminated groundwater well in the process of purifying contaminated groundwater present under the ground, measures the contamination distribution of the contaminated groundwater based on the monitoring result, controls a contaminated groundwater purification device, and predicts a purification period based on the measurement result, thereby efficiently purifying the contaminated groundwater.

14 Claims, 24 Drawing Sheets

(51) Int. Cl.
*G01N 21/31* (2006.01)
*G01N 21/33* (2006.01)
*G01N 21/3577* (2014.01)
*G01N 30/72* (2006.01)
*G01N 33/18* (2006.01)
*G06N 5/04* (2023.01)

(52) U.S. Cl.
CPC ..... *G01N 21/3577* (2013.01); *G01N 30/7206* (2013.01); *G01N 33/1813* (2013.01); *G01N 33/1833* (2013.01); *G06N 5/04* (2013.01); *C02F 2103/06* (2013.01); *C02F 2209/006* (2013.01); *C02F 2209/02* (2013.01); *C02F 2209/06* (2013.01); *C02F 2209/42* (2013.01)

(58) Field of Classification Search
CPC .............. C02F 2209/42; C02F 2101/20; C02F 2101/22; C02F 2101/322; C02F 2101/327; G01N 21/3103; G01N 21/33; G01N 21/3577; G01N 30/7206; G01N 33/1813; G01N 33/1833; G06N 5/04; Y02A 20/20

See application file for complete search history.

(56) References Cited

U.S. PATENT DOCUMENTS

2017/0044894 A1* 2/2017 Surowinski ........... E21B 47/047
2019/0297397 A1* 9/2019 Fleishman .............. H04L 67/12

FOREIGN PATENT DOCUMENTS

| KR | 10-1248848 B1 | 4/2013 |
| KR | 10-1267934 B1 | 5/2013 |
| KR | 10-1276538 B1 | 6/2013 |
| KR | 101271181 B1 * | 6/2013 |
| KR | 20160108635 A * | 9/2016 |
| KR | 10-1792808 B1 | 11/2017 |

OTHER PUBLICATIONS

Brennecke, Dennis, et al. "Microplastics as vector for heavy metal contamination from the marine environment." Estuarine, Coastal and Shelf Science 178 (2016): 189-195. (Year: 2016).*

* cited by examiner

IOT-BASED SYSTEM FOR MEASUREMENT OF CONTAMINATION DISTRIBUTION OF CONTAMINATED GROUNDWATER THROUGH REAL-TIME MONITORING OF CONTAMINATION DEGREE OF CONTAMINATED GROUNDWATER WELL FOR CONTROL OF CONTAMINATED GROUNDWATER PURIFICATION DEVICE AND PREDICTION OF PURIFICATION PERIOD BASED ON MEASUREMENT RESULT

FIELD OF THE INVENTION

The present invention relates to an IoT-based system for measurement of contamination distribution of contaminated groundwater through real-time monitoring of a contamination degree of a contaminated groundwater well for control of a contaminated groundwater purification device and prediction of a purification period based on the measurement result, and more particularly to an IoT-based system for measurement of contamination distribution of contaminated groundwater through real-time monitoring of a contamination degree of a contaminated groundwater well for control of a contaminated groundwater purification device and prediction of a purification period based on the measurement result, which monitors a groundwater well in real time based on sensor data collected from the contaminated groundwater well in the process of purifying contaminated groundwater present under the ground, measures the contamination distribution of the contaminated groundwater based on the monitoring result, controls a contaminated groundwater purification device, and predicts a purification period based on the measurement result, thereby efficiently purifying the contaminated groundwater.

BACKGROUND OF THE INVENTION

In general, groundwater is water that is formed when a portion of rainwater permeates into the cracks in soil from the ground surface, reaches a layer that does not transmit water, and collects in the layer. Moisture also exists above the groundwater table. In the case in which the channels in the soil are small, the groundwater rises toward the surface layer as capillary water, and is absorbed in the roots of plants. Groundwater may be seriously contaminated within a short time period by nearby military camps, gas stations, factories, or the like. Thus, groundwater in an area with contaminated soil needs to be purified immediately. Examples of commonly used groundwater purification methods include a method of excavating and taking out contaminated soil and pumping contaminated groundwater, a method of digging an injection well and an extraction well in a contaminated area to extract contaminants and inject microorganisms, nutrients, and chemical treatment agents, and the like.

In this case, during the purification process, it is required to automatically adjust the amount of a purification agent that is injected in consideration of a degree of contamination and to inject the purification agent in the direction in which contaminants move along the flow of groundwater.

In addition, because the elution and movement of contaminants of groundwater into the surrounding medium is invisible and complicated, it is very difficult to observe the range and degree of contamination and to predict the movement of contaminants. Therefore, monitoring and tracing the range and degree of contamination is required.

In addition, the purification process is controlled in consideration of various physical, chemical and biological characteristics of soil and groundwater. Therefore, in order to predict the movement of contaminants and to successfully purify soil and groundwater, it is important to accurately understand the physical characteristics (e.g. density, water permeability, water content, diffusion, flow rate, etc.), the chemical characteristics (e.g. pH, electrical conductivity, oxidation-reduction potential, cation exchange ability, organic carbon/nitrogen, organic matter content, etc.), and the biological characteristics (e.g. microbial species/community distribution, biomass, etc.) of the soil and the groundwater through sampling and monitoring thereof and to perform the purification process based on the sampling and monitoring results.

In addition, during the process of purifying contaminated groundwater existing under the ground, it is essential not only to monitor the degree of contamination of the groundwater and the degree of purification thereof in real time, but also to predict the total purification period required for complete purification by checking the degree of contamination after a certain period of time.

In addition, there is the need to develop a system for automatically controlling a purification device capable of adjusting the amount of pumped groundwater and controlling the purification process by checking the range and degree of contamination and monitoring the purification process in real time.

Hereinafter, some examples of conventional technology related to a system for monitoring the degree of contamination of a groundwater well in real time and controlling a contaminated groundwater purification device will be described. Korean Patent Registration No. 10-1248848 (Mar. 25, 2013) discloses a system for monitoring soil and groundwater environments in real time. The system includes a state measurement sensor unit, which is installed at at least one observation site and measures the states of soil and groundwater at the observation site to generate state information, an observation site monitoring unit, which is connected to the state measurement sensor unit and monitors the state information, a remote monitoring server, which receives the state information monitored by each observation site monitoring unit and provides the state information to a user through a user interface (UI), and at least one portable terminal, which is registered in the remote monitoring server and receives a message. The observation site monitoring unit includes a state information collection unit, which receives and stores the state information generated by the state measurement sensor unit in real time and at the same time transmits the stored state information to the remote monitoring server, an observation site information storage unit, which stores information about the surroundings of the observation site, an information provision unit, which provides the state information and the information about the surroundings, an operation mode control unit, which controls the state information collection unit and the information storage unit to selectively provide the state information or the information about the surroundings to the information provision unit in accordance with an administrator mode or a user mode, and a power supply unit, which supplies power to the state measurement sensor unit and the observation site monitoring unit. The state information collection unit includes a state information storage module, which stores the state information received from the state measurement sensor unit, a communication module, which wirelessly transmits the state information stored in the state information storage module to the remote monitoring server, a control module, which controls the state measurement sensor unit to operate according to a set input value including any one of a time, a temperature, and a rainfall, and turns on and off the state measurement sensor unit so as to minimize power consumption, and a state information comparison module, which compares the state information generated by the state measurement sensor unit with preset state information. When the state information generated by the state measurement sensor unit falls outside of a predetermined range of preset state information, the state information comparison module transmits an alarm to the remote monitoring server through the communication module. Alternatively, the state information comparison module compares the generated state information with each of a plurality of pieces of preset user-based state information. When the generated state information falls outside of a predetermined range of the preset user-based state information, the state information comparison module transmits a corresponding user-based alarm to the remote monitoring server so that an alarm message is sent to a corresponding one of the portable terminals registered in the remote monitoring server in advance. When the observation site monitoring unit is operated in a user mode, the operation mode control unit controls the information provision unit to display the state information and the information about the surroundings. When the observation site monitoring unit is operated in an administrator mode, the operation mode control unit controls the information provision unit to enable an administrator to edit the state information and the information about the surroundings, which are stored in the state information collection unit and the observation site information storage unit, respectively.

Korean Patent Registration No. 10-0978939 (Aug. 24, 2010) discloses a remote monitoring system for purifying multiple-contaminated groundwater. The system includes a multiple-contaminated groundwater purification device, a remote terminal device, a wired-wireless network, a communication control device (or a field interface unit (FIU)), and a centralized remote monitoring control system. The multiple-contaminated groundwater purification device includes a sediment-oil-water separation tank, into which deep-well groundwater or excavated groundwater contaminated with various contaminants such as organic contaminants and heavy metals is pumped and which separates sand having high specific gravity and/or inorganic impurities contained in the contaminated groundwater pumped into an inflow pipe using gravity and removes at least one kind of oil selected from the group consisting of diesel, kerosene, and total petroleum hydrocarbon (TPH), a water collection tank, which temporarily stores the contaminated groundwater introduced thereinto at a predetermined water level, a chemical-reaction/inclination-plate settling tank, which mixes at least one heavy metal selected from the group consisting of Al, Fe, Cr, Cd, Cu, Pb, Hg, As, Ni, and Zn, CN, normal-hexane (n-Hexane), an extract, a suspended material (SS), or a precipitate, which is contained in the contaminated groundwater introduced from the water collection tank, with a chemical supplied from a chemical storage tank in a chemical reaction unit, thereby depositing and removing the above material through chemical reaction, neutralization, and cohesion, and which deposits and removes a fine precipitate using an inclination plate of an inclination plate settling unit, a floatation deaeration tank, which injects microbubbles generated by a low-pressure microbubble generation device into the contaminated groundwater introduced from the chemical-reaction/inclination-plate settling tank, diffuses the same to a floatation unit of the floatation deaeration tank in order to separate at least one kind of oil selected from the group consisting of diesel, kerosene, and total petroleum hydrocarbon (TPH), at least one volatile organic compound (VOC) selected from the group consisting of BTEX (benzene, toluene, ethyl benzene, and xylene), phenol, trichloroethylene (TCE), and perchloroethylene (PCE), a remaining fine suspended material (SS), or an n-Hexane extract through floatation, deaerates the VOC by maximizing the specific surface area thereof using a deaeration unit, including a horizontal stripper filled with polypropylene packings and a demister, and thereafter adsorbs the VOC using activated carbon in an activated carbon tower, and an advanced oxidation process tank, which is particularly used to process the groundwater introduced from the floatation deaeration tank to a quality corresponding to residential water, the advanced oxidation process tank being configured to inject ozone (O3) into the groundwater in order to perform purification, such as an oxidation process, color removal, and deodorization, on a remaining fine n-Hexane extract, at least one kind of oil selected from the group consisting of diesel, kerosene, and total petroleum hydrocarbon (TPH), and/or at least one volatile organic compound (VOC) selected from the group consisting of BTEX (benzene, toluene, ethyl benzene, and xylene), phenol, trichloroethylene (TCE), and perchloroethylene (PCE) through an ozone advanced oxidation process (ozone AOP), thereby reinjecting or discharging the purified groundwater into the corresponding site. The remote terminal device is connected to a controller, a monitoring camera, and a water-quality measurement instrument, which are mounted to at least one of the sediment-oil-water separation tank, the water collection tank, the chemical-reaction/inclination-plate settling tank, the floatation deaeration tank, or the advanced oxidation process tank of the multiple-contaminated groundwater purification device, and transmits data to the centralized remote monitoring control system or receives a control command from the centralized remote monitoring control system, thereby performing real-time control. The wired-wireless network is connected to a data communication unit of the remote terminal device and performs data communication therewith. The communication control device (or the field interface unit (FIU)) is connected to the wired-wireless network and relays the data communication between the remote terminal device and the centralized remote monitoring control system. The centralized remote monitoring control system includes a remote administrator interface, which transmits information about the multiple-contaminated groundwater purification device to the administrator or receives information from the administrator.

Korean Patent Registration No. 10-1792808 (Oct. 26, 2017) discloses a contaminated groundwater remote control in-situ treatment system. The system includes an extraction step (S100) of extracting groundwater from the ground, a separation step (S200) of separating a liquid phase and a gas phase in the extracted groundwater using a gas-liquid separator, a monitoring step (S300) of monitoring the separated extraction water, an information transmission step (S400) of transmitting the monitored information to a controller, an analysis step (S500) of analyzing the transmitted information, a purification agent injection step (S600) of injecting a purification agent according to the analyzed information, an extracted groundwater treatment step (S700) of purifying the extracted groundwater that has been completely analyzed through monitoring, a nanoscale zero-valent iron collection step (S800) of collecting nanoscale zero-valent iron from the treated groundwater through magnetic separation, a discharge step (S900) of discharging the completely purified groundwater, and a management step (S1000) of organizing the above steps by sheets and managing the same. The monitoring step (S300) includes TPH monitoring, TVOCs monitoring, BTEX, TCE and PCE monitoring, and nitrate/ammonium monitoring. In the purification agent injection step (S600), nanoscale zero-valent iron, a microorganism, a nutrient, an oxidizing agent, a catalyst, or a surfactant is selectively injected as the purification agent in consideration of the type of contaminant and the characteristics of the soil. In the extracted groundwater treatment step (S700), the gas and the liquid separated by the gas-liquid separator are monitored through a gas analyzer and a water quality analyzer, respectively. The gas is collected in an adsorption tower using activated carbon so that a pollution concentration thereof is reduced, and is discharged into the atmosphere. The liquid undergoes water treatment in the purification agent injection step (S600). In the nanoscale zero-valent iron collection step (S800), nanoscale zero-valent iron contained in the injected purification agent is collected through magnetic separation from the treated groundwater that has passed through the extracted groundwater treatment step (S700). The extracted groundwater in a sampling tank, which has been completely monitored, and extra groundwater in a drain tank are transferred to the water treatment system. The water treatment system is constituted by a nano-reactor and a magnetic separation collection device. Nanoscale zero-valent iron, the surface of which is modified by CMC-nZVI (CMC (carboxylmethyl cellulose)), which is a purification agent, nanoscale zero-valent iron, the surface of which is modified by TPPnFe0 (TPP (tetrapolyphosphate)), bio-magnetite (magnetite produced using *Clostridium* sp.), bio-FeS (FeS synthesized by indigenous microorganisms using mine tailings from a decommissioned mine), nano-Fe3O4, Fe3O4@MAA (methacrylic acid), Fe3O4@Al(OH)3, Fe3O4@SiO2, a microorganism, a nutrient, an oxidizing agent, a catalyst, or a surfactant is selectively injected in consideration of the type of contaminant and the characteristics of the soil. The groundwater reacts with nanoscale zero-valent iron in the nano-reactor to be purified, and is transferred to the magnetic separation collection device. The nanoscale zero-valent iron is collected through the magnetic separation collection device, and is transferred to a chemical tank in an automatic purification agent injection system to be recycled. The management step (S1000) is a step of organizing the steps (S100 to S900) by sheets and managing the same. In the management step (S1000), the data analyzed by the gas analyzer and the water quality analyzer in the monitoring step (S300) is collected and analyzed, and it is possible to receive data and to control injection of the purification agent at a purification site using a control PC, in which a PLC program is installed, in the purification agent injection step (S600) in consideration of the analyzed information. Further, it is also possible to remotely receive data and perform control via a smartphone even if a worker is not at the purification site.

Korean Patent Registration No. 10-1276538 (Jun. 13, 2013) discloses an apparatus for purifying contaminated soil. The apparatus includes a plurality of wells installed in contaminated soil, an air injection device, a liquid chemical supply device, a contaminant extraction device, a switch valve box, a main header, and a monitoring unit. The air injection device includes an air compressor, which is installed outside each of the wells and generates compressed air to inject the compressed air into each of the wells so that fine cracks are formed in a contaminated soil by the air pressure, a blower configured to increase the pressure of the compressed air and to supply the same to each of the wells, and a motor configured to drive the blower. The liquid chemical supply device includes a liquid chemical tank, which is installed outside each of the wells and stores a liquid chemical in order to supply the liquid chemical to each of the wells to purify the contaminated soil through the fine cracks, and a liquid chemical supply pump configured to supply the liquid chemical to each of the wells. The contaminant extraction device includes a pumping motor, which is installed outside each of the wells and discharges contaminants and contaminated groundwater contained in the contaminated soil together with the liquid chemical used to purify the contaminated soil, a blower configured to generate pumping force for suctioning the contaminants and the contaminated groundwater from each of the wells and discharging the suctioned contaminants and contaminated groundwater to the outside using the driving force of the pumping motor, and a sludge tank configured to accommodate the contaminants and the contaminated groundwater transferred from each of the wells before the contaminants and the contaminated groundwater are transferred to the water treatment device to be purified. The switch valve box includes an opening/closing adjustment valve, which is mounted between each of the above devices and each of the wells and is opened or closed to allow or interrupt the flow of the air, the liquid chemical, and the contaminants that are introduced from each of the devices into corresponding wells or are discharged from each of the wells to corresponding devices. The main header includes a selective opening/closing valve, which is mounted between the switch valve box and each of the wells and selectively opens or closes a corresponding one of a plurality of flow lines in order to inject the air and the liquid chemical to each of the wells or to discharge the contaminants in response to the opening or closing of the opening/closing adjustment valve of the switch valve box. The monitoring unit is connected to each of the devices and the opening/closing adjustment valve of the switch valve box, detects the pressure in each of the wells, and controls the injection of the air and the liquid chemical into each of the wells and the discharge of the contaminants in accordance with the detected pressure. The monitoring unit includes a digital pressure gauge, which receives a sensing signal from a sensor connected to each well and continuously measures a change in the pressure in each well at intervals of 1 second or more, a data collection unit, which is connected to the digital pressure gauge, receives pressure values measured by the digital pressure gauge, and converts the received pressure values to data, a reference value data unit, which stores data on the reference pressure value of each well, a comparison unit, which is connected to the data collection unit and the reference value data unit and compares the measured value data of the data collection unit with the reference value data of the reference value data unit, a controller, which is connected to the comparison unit and controls each of the devices and various other components in response to the comparison data of the comparison unit, and a display unit, which is connected to the controller and enables verification of the state of each of the constituent components of the monitoring unit from the outside.

In addition, as conventional technology similar to technology related to a method of detecting a degree of contamination during the process of purifying contaminated groundwater and predicting the total purification period required for complete purification, Korea Patent Registration 10-1267934 (May 21, 2013) discloses a method of predicting the movement route of a groundwater contamination source. The method includes an initial setting step of setting an underground area of interest in which non-aqueous phase liquid (NAPL), acting as a groundwater contamination source, moves, dividing the area of interest into a plurality of cells, and setting initial conditions of the groundwater, the NAPL and a surfactant for increasing the solubility of the NAPL in the groundwater, a multiphase flow determination step of calculating the degree of saturation and the Darcy's velocity of the groundwater in each cell at predetermined time intervals, calculating the total fluid pressure of the groundwater and the NAPL in the pores in each cell using the phase transfer of the NAPL, which is dissolved in the groundwater and is moved, calculating the total fluid velocity of the groundwater and the NAPL in each cell using the total fluid pressure, calculating the degree of saturation of the groundwater in the pores using the total fluid velocity, and calculating the final velocity of the groundwater in the pores, and a multispecies contaminant transport determination step of calculating the concentration of the NAPL dissolved in the groundwater in each cell at the predetermined time intervals using the Darcy's velocity and the degree of saturation of the groundwater calculated at the predetermined time intervals in the multiphase flow determination step.

However, the conventional technology disclosed in the above-described patent documents merely relates to real-time monitoring of soil and groundwater environments prior to purification of contaminated groundwater, monitoring of the state of groundwater in each cell, monitoring of the purification state of soil and groundwater during a purification process, or remote control for in-situ purification of contaminated groundwater. None of the above patent documents discloses an IoT-based system for measurement of contamination distribution of contaminated groundwater through real-time monitoring of a contamination degree of a contaminated groundwater well for control of a contaminated groundwater purification device and prediction of a purification period based on the measurement result, which monitors a groundwater well in real time based on sensor data collected from the contaminated groundwater well in the process of purifying contaminated groundwater present under the ground, measures the contamination distribution of the contaminated groundwater based on the monitoring result, controls a contaminated groundwater purification device, and predicts a purification period based on the measurement result, thereby efficiently purifying the contaminated groundwater. To date, there has been no control system capable of simultaneously performing real-time monitoring of contaminated groundwater in each cell, measurement of contamination distribution of contaminated groundwater, control of a contaminated groundwater purification device, and purification period prediction.

SUMMARY OF THE INVENTION

Therefore, the present invention has been made in view of the above problems, and it is an object of the present invention to provide an IoT-based system for measurement of contamination distribution of contaminated groundwater through real-time monitoring of a contamination degree of a contaminated groundwater well for control of a contaminated groundwater purification device and prediction of a purification period based on the measurement result, which monitors a groundwater well in real time based on sensor data collected from the contaminated groundwater well in the process of purifying contaminated groundwater present under the ground, measures the contamination distribution of the contaminated groundwater based on the monitoring result, controls a contaminated groundwater purification device, and predicts a purification period based on the measurement result, thereby efficiently purifying the contaminated groundwater.

In accordance with the present invention, the above and other objects can be accomplished by the provision of an IoT-based system for measurement of contamination distribution of contaminated groundwater through real-time monitoring of a contamination degree of a contaminated groundwater well for control of a contaminated groundwater purification device and prediction of a purification period based on the measurement result, the IoT-based system including a sensor unit mounted in each of a plurality of wells excavated to purify contaminated groundwater, the sensor unit including a contamination degree sensor for measuring a degree of contamination by contaminants, a pH sensor, a temperature sensor, a water level sensor, a pumping amount sensor, and a rainfall sensor, a server unit configured to collect sensor data transmitted from the sensor unit and to classify the sensor data based on a data type, and a web dashboard unit configured to display the sensor data transmitted from the server unit to enable a user to verify or control the desired sensor data on a well basis and on a data-type basis in real time. The web dashboard unit includes a purification-area-based status screen, a main screen, a contamination degree screen, a pumping amount screen, a groundwater level screen, an indirect purification factor screen, a contaminated-area-sensor-data-based movement distribution history screen, a distribution comparison screen, a purification control screen including a sensor-data-type selection window enabling selection of the type of sensor data, the sensor-data-type selection window being displayed in a contamination map screen, in which a range of a contaminated area, a depth of contamination, a value of each type of sensor data on a well basis, a two-dimensional or three-dimensional potentiometric surface map based on the value of each type of sensor data, the location of the purification device, the locations of the wells, and connection pipes are displayed on a contaminated area map, and a purification period prediction screen displaying a change in the value of each type of sensor data in the contaminated area.

The contaminated groundwater may be purified such that the contaminated groundwater is pumped from the plurality of wells and is purified on the ground by the purification device or such that a purification agent is injected into each of the plurality of wells and the contaminated groundwater mixed with the purification agent is pumped and purified by the purification device.

The contaminants may include petroleum-based contaminants including benzene, toluene, xylene, ethyl benzene, total petroleum hydrocarbon (TPH), trichloroethylene (TCE), tetrachloroethylene (PCE), organophosphorus compound, PCB, cyan, and phenol, and heavy metal contaminants including arsenic, lead, cadmium, hexavalent chromium, copper, mercury, zinc, nickel, and fluorine.

The contamination degree sensor may be selectively implemented, depending on the contaminants, as any of analysis devices including a gas chromatograph (GC), a gas chromatography-mass spectrometer (GC-MS), an atomic absorption spectrophotometer, an atomic emission spectrophotometer, an absorption spectrophotometer, an infrared spectrophotometer, and an ultraviolet spectrophotometer.

The contamination degree sensor may measure the degree of contamination using the contaminated groundwater sampled from the wells.

The purification-area-based status screen may include a status screen displaying a construction project name, a construction period, types of contaminants, the cause of contamination, the purification standard, and a purification promotion history, and a contamination map screen, in which a range of a contaminated area, a depth of contamination, the location of the purification device, the locations of the wells, and connection pipes are displayed on the contaminated area map.

The main screen may include a sensor-data-type selection window enabling selection of the type of sensor data, and may display the value of each type of sensor data selected from each of the plurality of wells and a two-dimensional or three-dimensional potentiometric surface map based on the value of each type of sensor data on the contaminated area map.

The contamination degree screen may include a contaminant-type selection window enabling selection of the type of contaminant, a contamination modeling diagram, in which the degree of contamination by the contaminant selected from each of the plurality of wells and a two-dimensional or three-dimensional potentiometric surface map of the contaminant based on the degree of contamination by the contaminant are displayed on the contaminated area map, a contamination degree chart indicating a numerical change in the degree of contamination by the contaminant selected from each of the plurality of wells, and a contamination data table indicating the degree of contamination by the selected contaminant on a well basis and on a date basis.

The pumping amount screen may include a pumping amount modeling diagram, in which the amount pumped from each of the plurality of wells, a two-dimensional or three-dimensional potentiometric surface map of the pumping amount based thereon, and a degree of contamination by the contaminant selected from each of the plurality of wells are displayed on the contaminated area map, a pumping amount chart indicating a change in the amount pumped from each of the plurality of wells, and a pumping amount data table indicating the pumping amount on a well basis and on a date basis.

The groundwater level screen may include a groundwater level modeling diagram, in which a groundwater level in each of the plurality of wells, a two-dimensional or three-dimensional potentiometric surface map of the groundwater level based thereon, and a groundwater flow direction diagram are displayed on the contaminated area map, a strata section diagram indicating the groundwater level displayed on the contaminated area map and the strata in a sectional manner, and a groundwater level data table indicating the groundwater level on a well basis and on a date basis.

The indirect purification factor screen may include an indirect purification factor modeling diagram, in which values of indirect purification factors including temperature, pH, and rainfall in each of the plurality of wells and a two-dimensional or three-dimensional potentiometric surface map of the indirect purification factors based thereon are displayed on the contaminated area map, an indirect purification factor chart indicating a change in the values of the indirect purification factors in each of the plurality of wells, and an indirect purification factor data table indicating the values of the indirect purification factors on a well basis and on a date basis.

When each of the plurality of wells in the main screen is clicked and selected, the diameters and depths of the wells and the specifications of the pumps may be displayed on a well basis.

When each of the plurality of wells in the main screen is clicked and selected, a graph indicating a numerical change in each type of sensor data may be displayed.

When the peak of the graph displayed in each of the contamination degree chart in the contamination degree screen, the pumping amount chart in the pumping amount screen, and the indirect purification factor chart in the indirect purification factor screen is clicked and selected, the degree of contamination of each contaminant, the pumping amount, and the value of each indirect purification factor on the corresponding date may be displayed.

The distribution history screen may include a sensor-data-type selection window enabling selection of the type of sensor data, the sensor-data-type selection window being displayed in a contamination map screen, in which a range of a contaminated area, a depth of contamination, a value of each type of sensor data on a well basis, a two-dimensional or three-dimensional potentiometric surface map based on the value of each type of sensor data, the location of the purification device, and the locations of the wells are displayed on a contaminated area map, may further include a period slide bar enabling selection of a start date and an end date, and may display a change history of the selected sensor data during a selected period, the change history of the selected sensor data including a range of a contaminated area, a depth of contamination, a value of each type of sensor data on a well basis, and a two-dimensional or three-dimensional potentiometric surface map based on the value of each type of sensor data.

The distribution comparison screen may include a sensor-data-type selection window enabling selection of the type of sensor data and a plurality of comparison screens split on a period basis, in each of which a change history of the selected sensor data, which includes a range of a contaminated area, a depth of contamination, a value of each type of sensor data on a well basis, and a two-dimensional or three-dimensional potentiometric surface map based on the value of each type of sensor data, is displayed on a contaminated area map.

When a purification device in the purification control screen is clicked and selected, a purification device operation screen may be displayed. The purification device operation screen may include an entire construction diagram of the purification device in each purification zone, a flow indicator indicating the flow of contaminated groundwater through the pipes of the purification device, reinjection into the wells, discharge into rainwater, and discharge into sewage, and an operation data table indicating the degree of contamination by the contaminants in each well, an amount pumped from each well, a water level in each well, a water level in the purification device, on/off of a pump in each well, on/off of a pump of the purification device, on/off of a pump supplying a chemical, and information about whether the purification device is operating normally.

The purification device operation screen may display a chart indicating the name of an injected chemical, the amount of the chemical that is injected, and a numerical change in the amount of the chemical that is injected.

On/off of the pump in each well, on/off of the pump of the purification device, and on/off of the pump supplying a chemical may be respectively controlled through the purification device operation screen.

When an inlet tank and an outlet tank of the purification device displayed in the purification device operation screen are respectively clicked and selected, a graph indicating a numerical change in the degree of contamination by the contaminants may be displayed.

The purification period prediction screen may include a sensor-data-type selection window enabling selection of the type of sensor data, the sensor-data-type selection window being displayed in a contamination map screen, in which a range of a contaminated area, a depth of contamination, a value of each type of sensor data on a well basis, a two-dimensional or three-dimensional potentiometric surface map based on the value of each type of sensor data, the location of the purification device, and the locations of the wells are displayed on a contaminated area map, may further include a period slide bar enabling selection of a start date and an end date, and may display a change history of the selected sensor data during a selected period, the change history of the selected sensor data including a range of a contaminated area, a depth of contamination, a value of each type of sensor data on a well basis, and a two-dimensional or three-dimensional potentiometric surface map based on the value of each type of sensor data.

The purification period prediction screen may be configured to enable verification of a contamination reduction state during the selected period based on the change history during the selected period.

The purification period prediction screen may be configured to output a predicted value of the degree of contamination after a predetermined period and a predicted value of the purification period. The predicted value of the degree of contamination after a predetermined period and the predicted value of the purification period may be calculated using a program executed based on a purification period prediction algorithm including the exponential function below:

$$C = C_0 e^{-kt}$$

where C indicates the degree of contamination (mg/L) of groundwater after a predetermined period, C0 indicates the initial degree of contamination (mg/L) of groundwater, k indicates the reduction coefficient (day$^{-1}$), and t indicates the time (day).

The predicted value of the degree of contamination after a predetermined period may be calculated such that the reduction coefficient k (day$^{-1}$) is calculated from the degree of contamination C (mg/L) of groundwater after a predetermined period (day) and the initial degree of contamination $C_0$ (mg/L) of groundwater, among the sensor data of the contamination degree sensor, a graph of the aforementioned exponential function is output, and the predicted value of the degree of contamination after a predetermined period (day) is calculated using the graph.

The predicted value of the purification period may be calculated such that the reduction coefficient k (day$^{-1}$) is calculated from the degree of contamination C (mg/L) of groundwater after a predetermined period (day) and the initial degree of contamination $C_0$ (mg/L) of groundwater, among the sensor data of the contamination degree sensor, a graph of the aforementioned exponential function is output, a contamination purification target is set using the graph, and a period within which it is required to accomplish the contamination purification target is calculated as the predicted value of the purification period.

The purification period prediction screen may display the amount of the chemical that is injected and the amount of power that is consumed during a selected period, and may calculate and display a predicted value of the amount of the chemical to be injected and a predicted value of the amount of power to be consumed during the period corresponding to the predicted value of the purification period using the program to which the purification period prediction algorithm is applied based on the amount of the chemical that is injected and the amount of power that is consumed.

A two-dimensional or three-dimensional potentiometric surface map of the sensor data, a two-dimensional or three-dimensional potentiometric surface map of each contaminant, a two-dimensional or three-dimensional potentiometric surface map of the pumping amount, a two-dimensional or three-dimensional potentiometric surface map of the groundwater level, or a two-dimensional or three-dimensional potentiometric surface map of each indirect purification factor may be configured to indicate numerical ranges such that the numerical ranges are distinguished by colors.

The IoT-based system for measurement of contamination distribution of contaminated groundwater through real-time monitoring of a contamination degree of a contaminated groundwater well for control of a contaminated groundwater purification device and prediction of a purification period based on the measurement result may be configured to allow a purification company or a supervisory institution to have online access thereto so as to perform verification or control.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
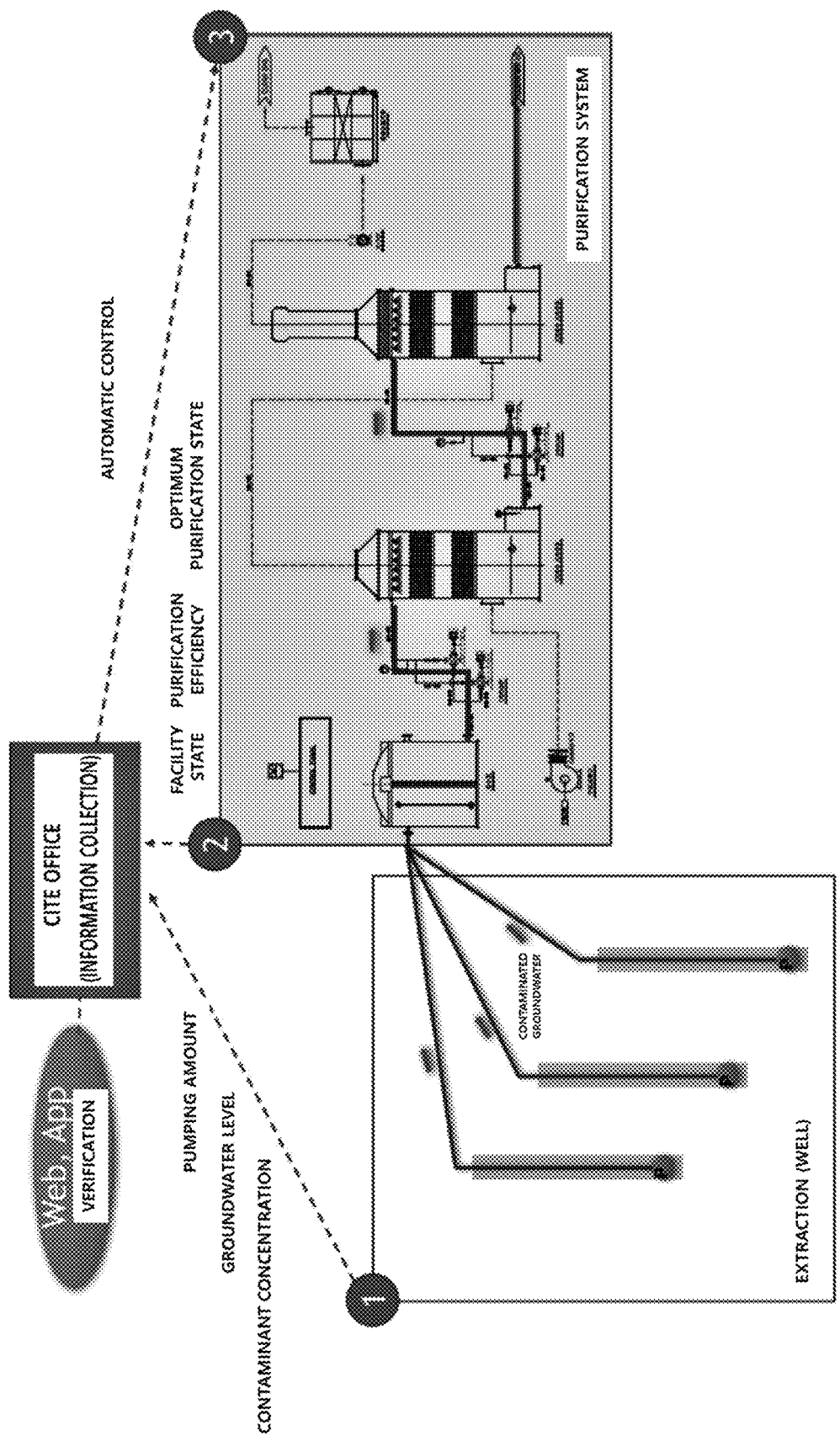
FIG. 1 is a schematic view showing the entire construction of an IoT-based system for measurement of contamination distribution of contaminated groundwater through real-time monitoring of a contamination degree of a contaminated groundwater well for control of a contaminated groundwater purification device and prediction of a purification period based on the measurement result according to the present invention.

Reference will now be made in detail to the preferred embodiments of the present invention, examples of which are illustrated in the accompanying drawings. The present invention may, however, be embodied in many different forms, and should not be construed as being limited to the embodiments set forth herein. Rather, these embodiments are provided so that this disclosure will be thorough and complete, and will fully convey the scope of the invention to those skilled in the art.

Referring to FIGS. 1 to 12, an IoT-based system for measurement of contamination distribution of contaminated groundwater through real-time monitoring of a contamination degree of a contaminated groundwater well for control of a contaminated groundwater purification device and prediction of a purification period based on the measurement result according to the present invention includes a sensor unit mounted in each of a plurality of wells excavated to purify contaminated groundwater, the sensor unit including a contamination degree sensor for measuring a degree of contamination by contaminants, a pH sensor, a temperature sensor, a water level sensor, a pumping amount sensor, and a rainfall sensor, a server unit configured to collect sensor data transmitted from the sensor unit and to classify the sensor data based on a data type, and a web dashboard unit configured to display the sensor data transmitted from the server unit to enable a user to verify or control the desired sensor data on a well basis and on a data-type basis in real time. The web dashboard unit includes a purification-area-based status screen, a main screen, a contamination degree screen, a pumping amount screen, a groundwater level screen, an indirect purification factor screen, a contaminated-area-sensor-data-based movement distribution history screen, a distribution comparison screen, a purification control screen including a sensor-data-type selection window enabling selection of the type of sensor data, the sensor-data-type selection window being displayed in a contamination map screen, in which a range of a contaminated area, a depth of contamination, a value of each type of sensor data on a well basis, a two-dimensional or three-dimensional potentiometric surface map based on the value of each type of sensor data, the location of the purification device, the locations of the wells, and connection pipes are displayed on a contaminated area map, and a purification period prediction screen displaying a change in the value of each type of sensor data in the contaminated area.

Here, the contaminated groundwater is purified such that the contaminated groundwater is pumped from the plurality of wells and is purified on the ground by the purification device or such that a purification agent is injected into each of the plurality of wells and the contaminated groundwater mixed with the purification agent is pumped and purified by the purification device.

In this case, the contaminants include petroleum-based contaminants including benzene, toluene, xylene, ethyl benzene, total petroleum hydrocarbon (TPH), trichloroethylene (TCE), tetrachloroethylene (PCE), organophosphorus compound, PCB, cyan, and phenol, and heavy metal contaminants including arsenic, lead, cadmium, hexavalent chromium, copper, mercury, zinc, nickel, and fluorine.

Figure 2:
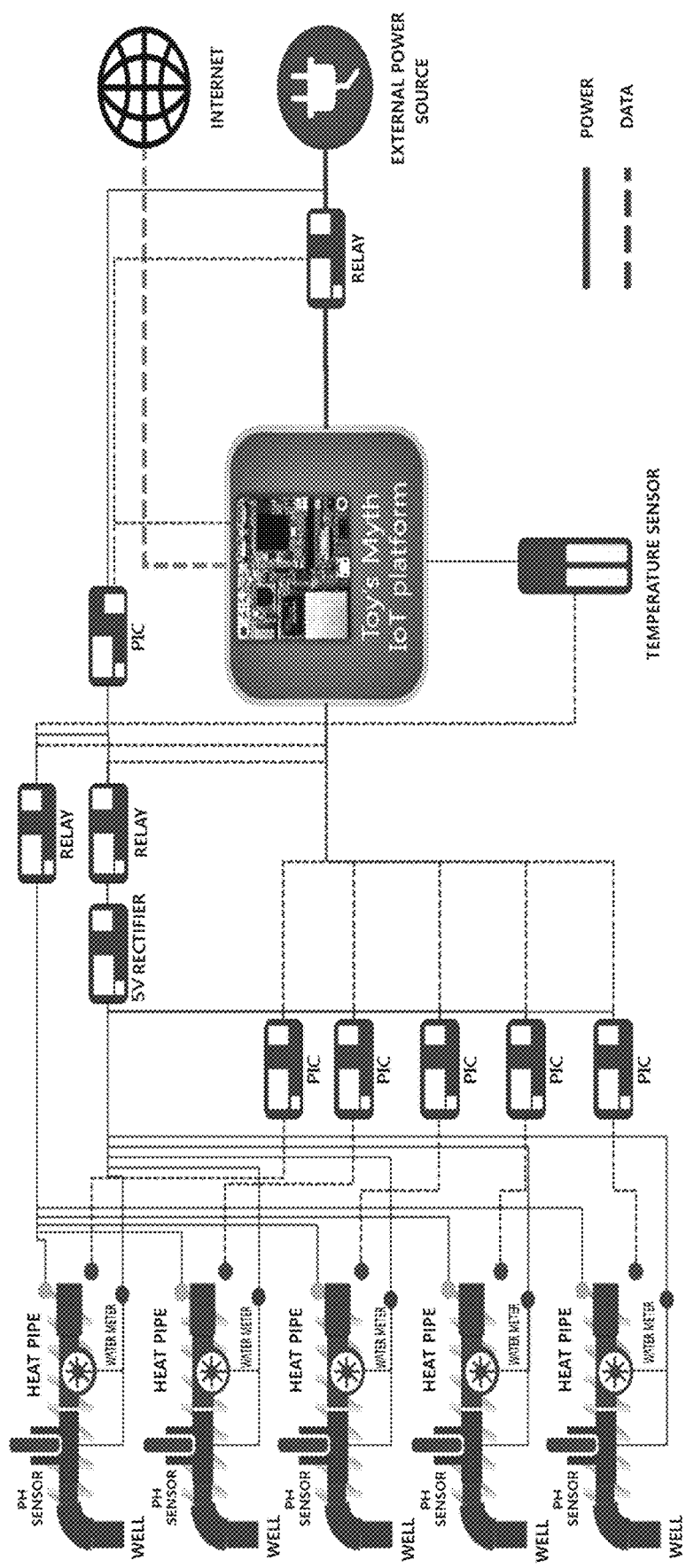
FIG. 2 is a diagram showing installation of wells in the entire construction of the IoT-based system for measurement of contamination distribution of contaminated groundwater through real-time monitoring of a contamination degree of a contaminated groundwater well for control of a contaminated groundwater purification device and prediction of a purification period based on the measurement result according to the present invention.

In addition, the contamination degree sensor is selectively implemented, depending on the contaminants, as any of analysis devices including a gas chromatograph (GC), a gas chromatography-mass spectrometer (GC-MS), an atomic absorption spectrophotometer, an atomic emission spectrophotometer, an absorption spectrophotometer, an infrared spectrophotometer, and an ultraviolet spectrophotometer. As shown in FIG. 2, the contamination degree sensor measures the degree of contamination using the contaminated groundwater sampled from the wells.

The web dashboard unit includes the purification-area-based status screen, the main screen, the contamination degree screen, the pumping amount screen, the groundwater level screen, and the indirect purification factor screen.

Figure 3:
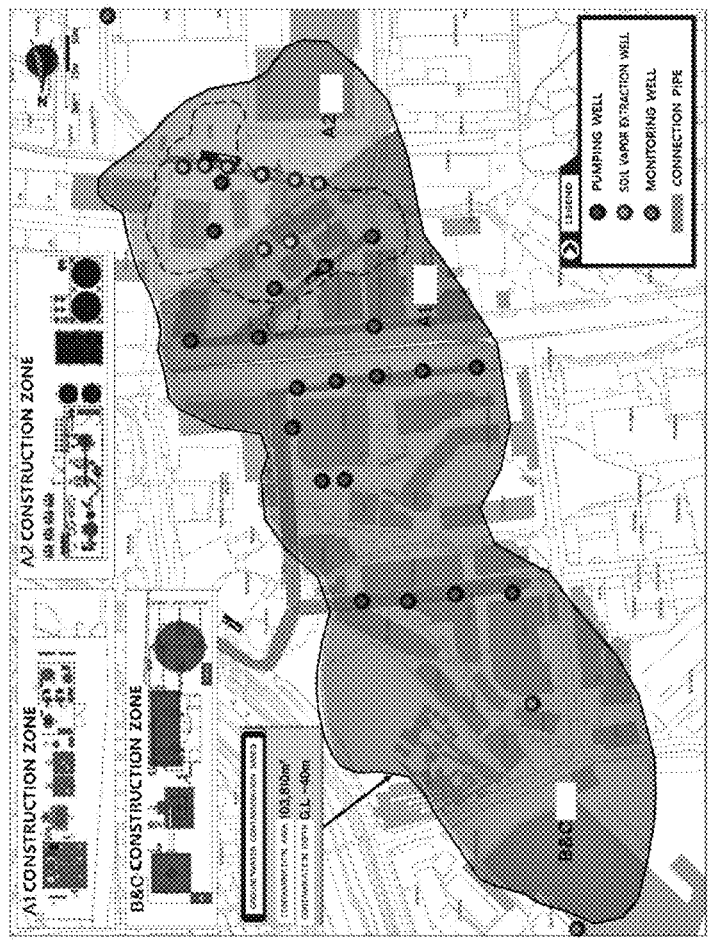
FIG. 3 is a purification-area-based status screen of a web dashboard unit of the IoT-based system for measurement of contamination distribution of contaminated groundwater through real-time monitoring of a contamination degree of a contaminated groundwater well for control of a contaminated groundwater purification device and prediction of a purification period based on the measurement result according to the present invention.

As shown in FIG. 3, the purification-area-based status screen includes a status screen displaying a construction project name, a construction period, types of contaminants, the cause of contamination, the purification standard, and a purification promotion history, and a contamination map screen, in which a range of a contaminated area, a depth of contamination, the location of the purification device, the locations of the wells, and connection pipes are displayed on the contaminated area map.

Figure 4:
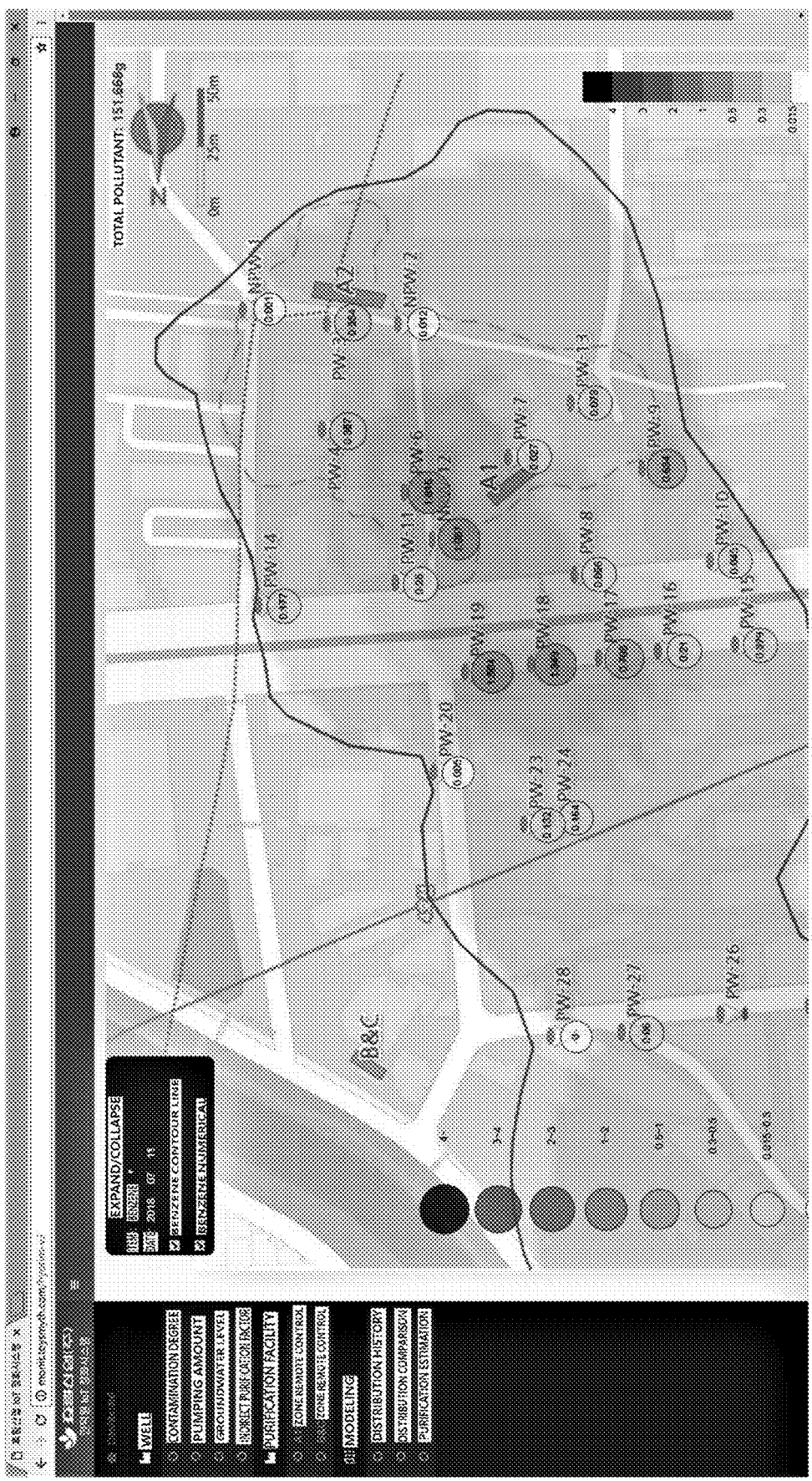
FIG. 4 is a main screen of the web dashboard unit of the IoT-based system for measurement of contamination distribution of contaminated groundwater through real-time monitoring of a contamination degree of a contaminated groundwater well for control of a contaminated groundwater purification device and prediction of a purification period based on the measurement result according to the present invention.
Figure 5:
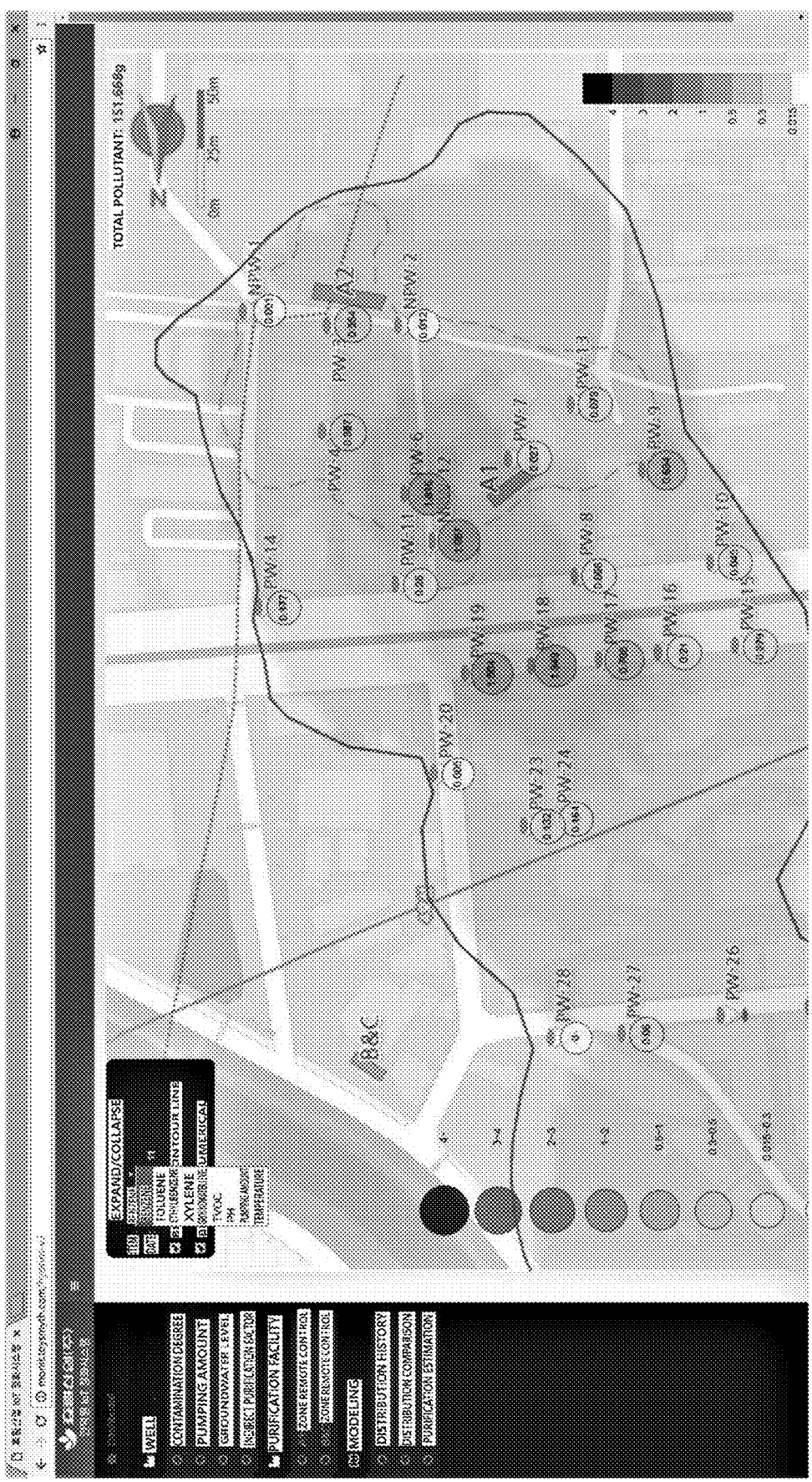
FIG. 5 is the main screen of the web dashboard unit of the IoT-based system for measurement of contamination distribution of contaminated groundwater through real-time monitoring of a contamination degree of a contaminated groundwater well for control of a contaminated groundwater purification device and prediction of a purification period based on the measurement result according to the present invention.

As shown in FIGS. 4 and 5, the main screen includes a sensor-data-type selection window enabling selection of the type of sensor data, and displays the value of each type of sensor data selected from each of the plurality of wells and a two-dimensional or three-dimensional potentiometric surface map based on the value of each type of sensor data on the contaminated area map.

Figure 6:
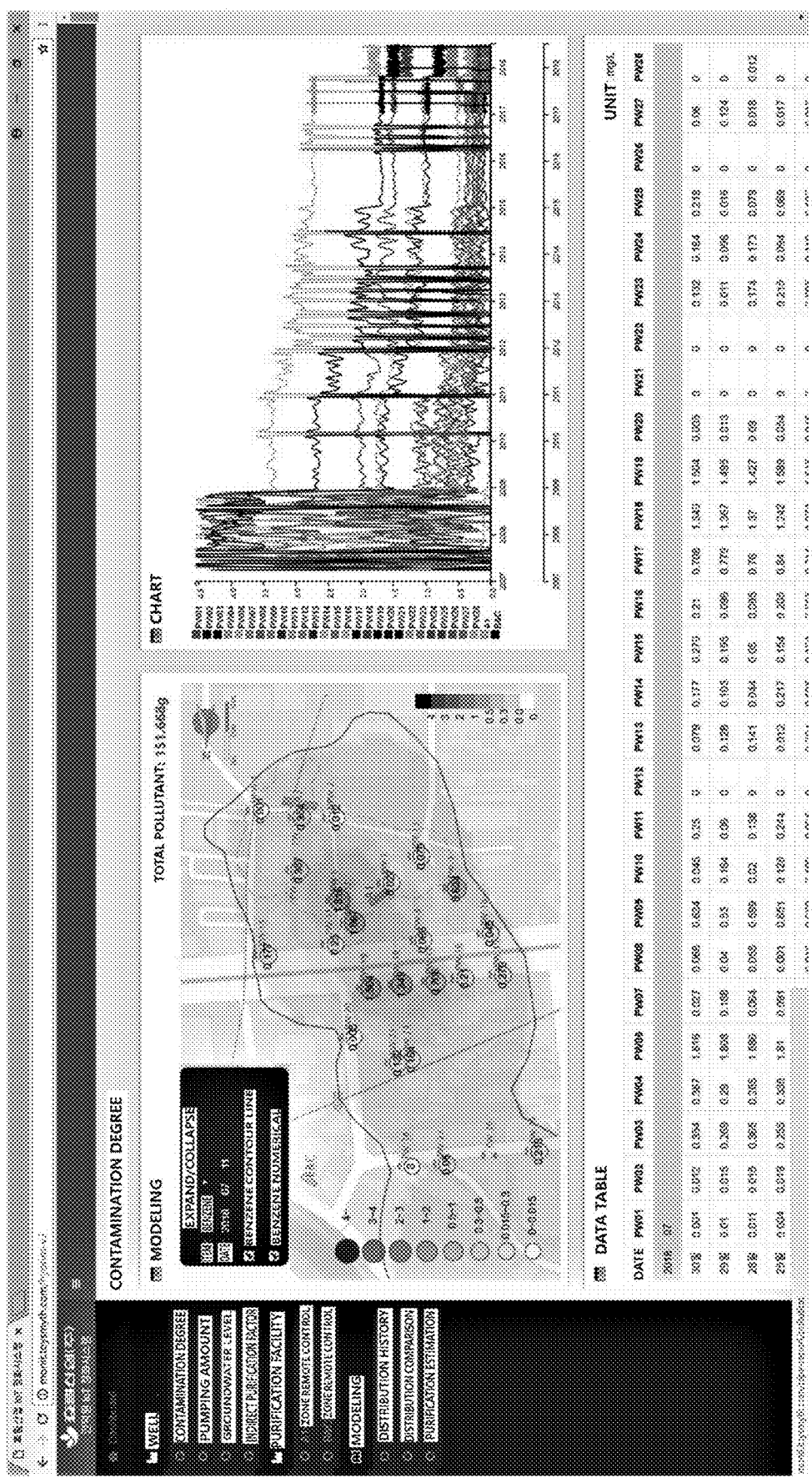
FIG. 6 is a contamination degree screen of the web dashboard unit of the IoT-based system for measurement of contamination distribution of contaminated groundwater through real-time monitoring of a contamination degree of a contaminated groundwater well for control of a contaminated groundwater purification device and prediction of a purification period based on the measurement result according to the present invention.
Figure 7:
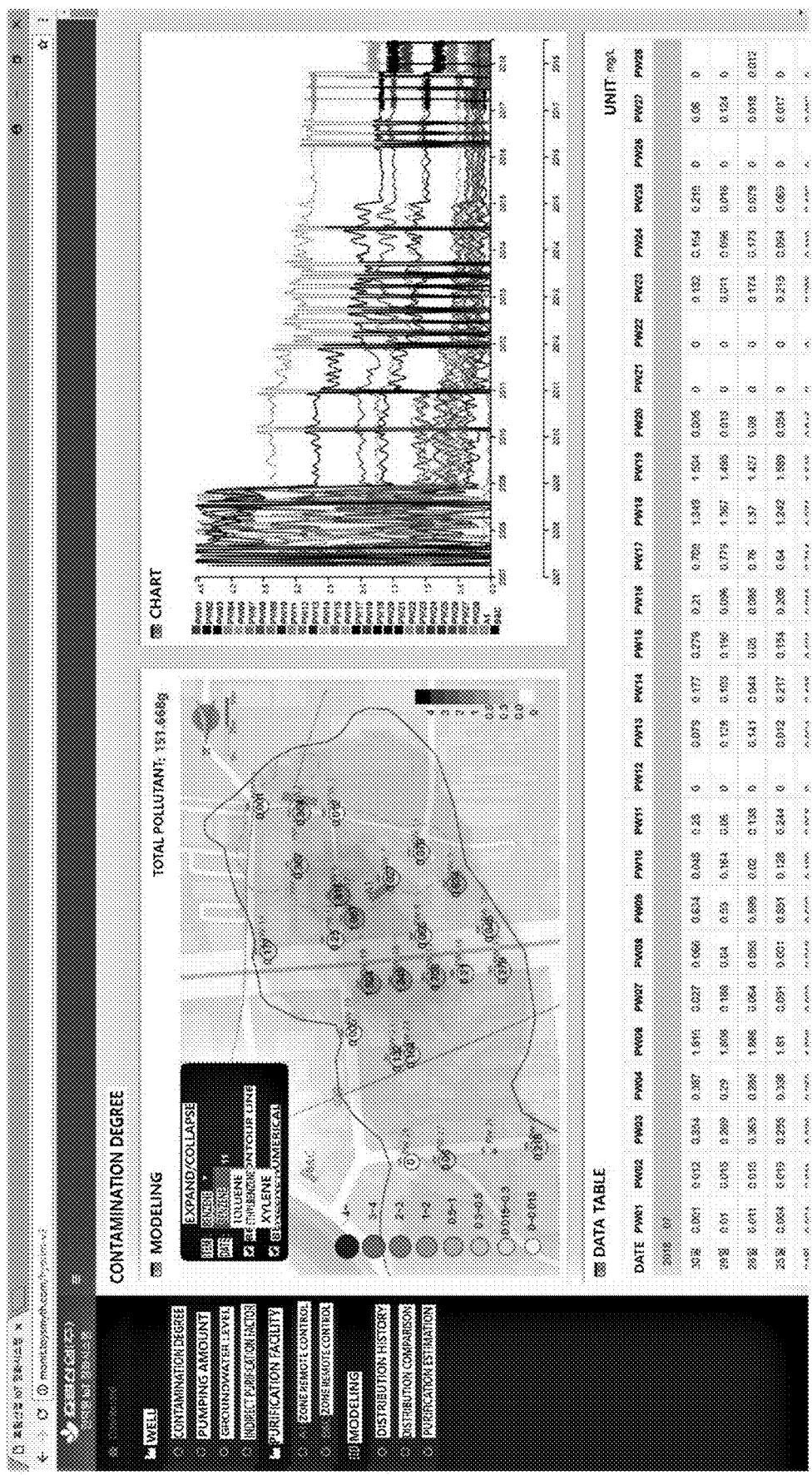
FIG. 7 is a contamination degree screen of the web dashboard unit of the IoT-based system for measurement of contamination distribution of contaminated groundwater through real-time monitoring of a contamination degree of a contaminated groundwater well for control of a contaminated groundwater purification device and prediction of a purification period based on the measurement result according to the present invention.

As shown in FIGS. 6 and 7, the contamination degree screen includes a contaminant-type selection window enabling selection of the type of contaminant, a contamination modeling diagram, in which the degree of contamination by the contaminant selected from each of the plurality of wells and a two-dimensional or three-dimensional potentiometric surface map of the contaminant based on the degree of contamination by the contaminant are displayed on the contaminated area map, a contamination degree chart indicating a numerical change in the degree of contamination by the contaminant selected from each of the plurality of wells, and a contamination data table indicating the degree of contamination by the selected contaminant on a well basis and on a date basis.

Figure 8:
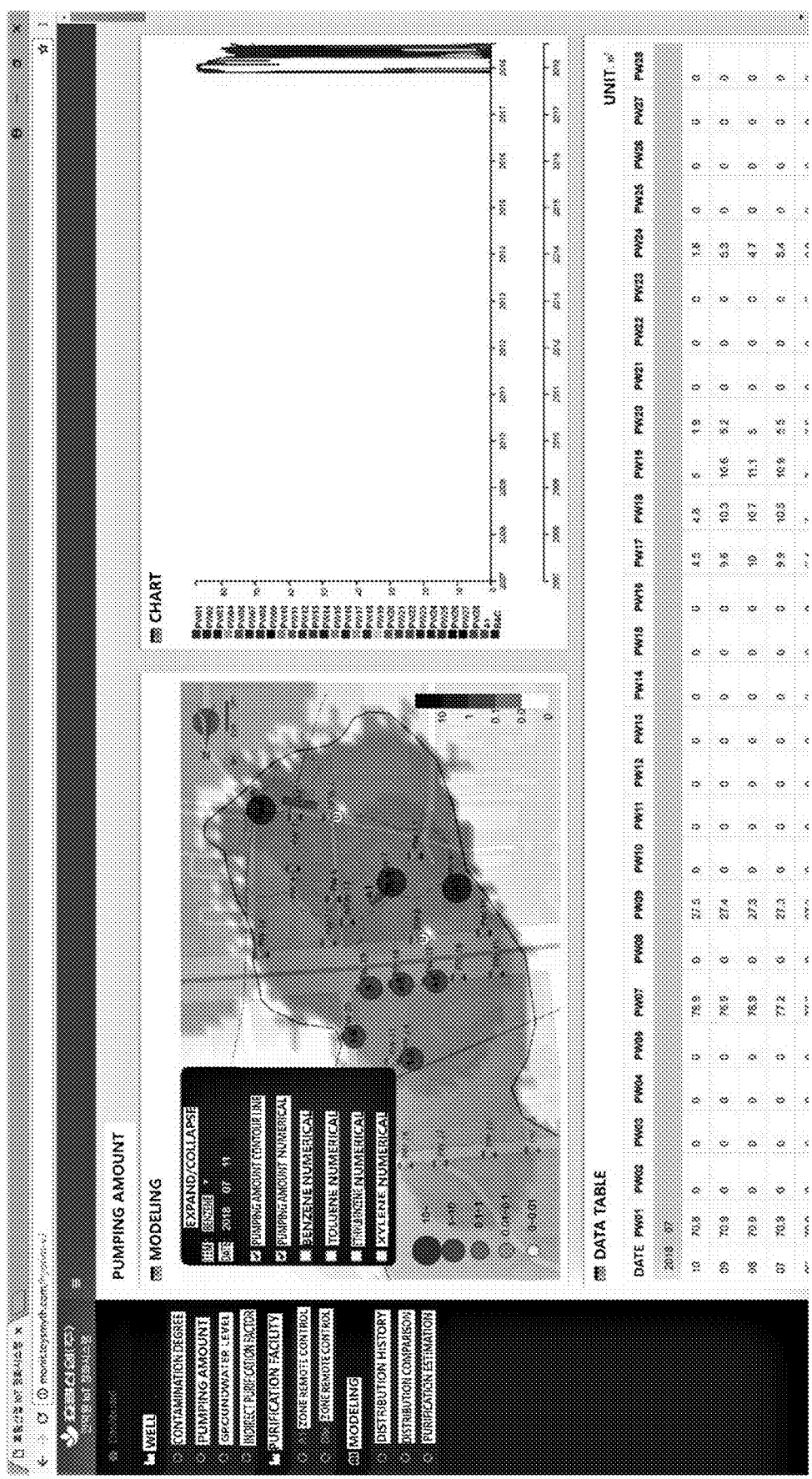
FIG. 8 is a pumping amount screen of the web dashboard unit of the IoT-based system for measurement of contamination distribution of contaminated groundwater through real-time monitoring of a contamination degree of a contaminated groundwater well for control of a contaminated groundwater purification device and prediction of a purification period based on the measurement result according to the present invention.

As shown in FIG. 8, the pumping amount screen includes a pumping amount modeling diagram, in which the amount pumped from each of the plurality of wells, a two-dimensional or three-dimensional potentiometric surface map of the pumping amount based thereon, and a degree of contamination by the contaminant selected from each of the plurality of wells are displayed on the contaminated area map, a pumping amount chart indicating a change in the amount pumped from each of the plurality of wells, and a pumping amount data table indicating the pumping amount on a well basis and on a date basis.

Figure 9:
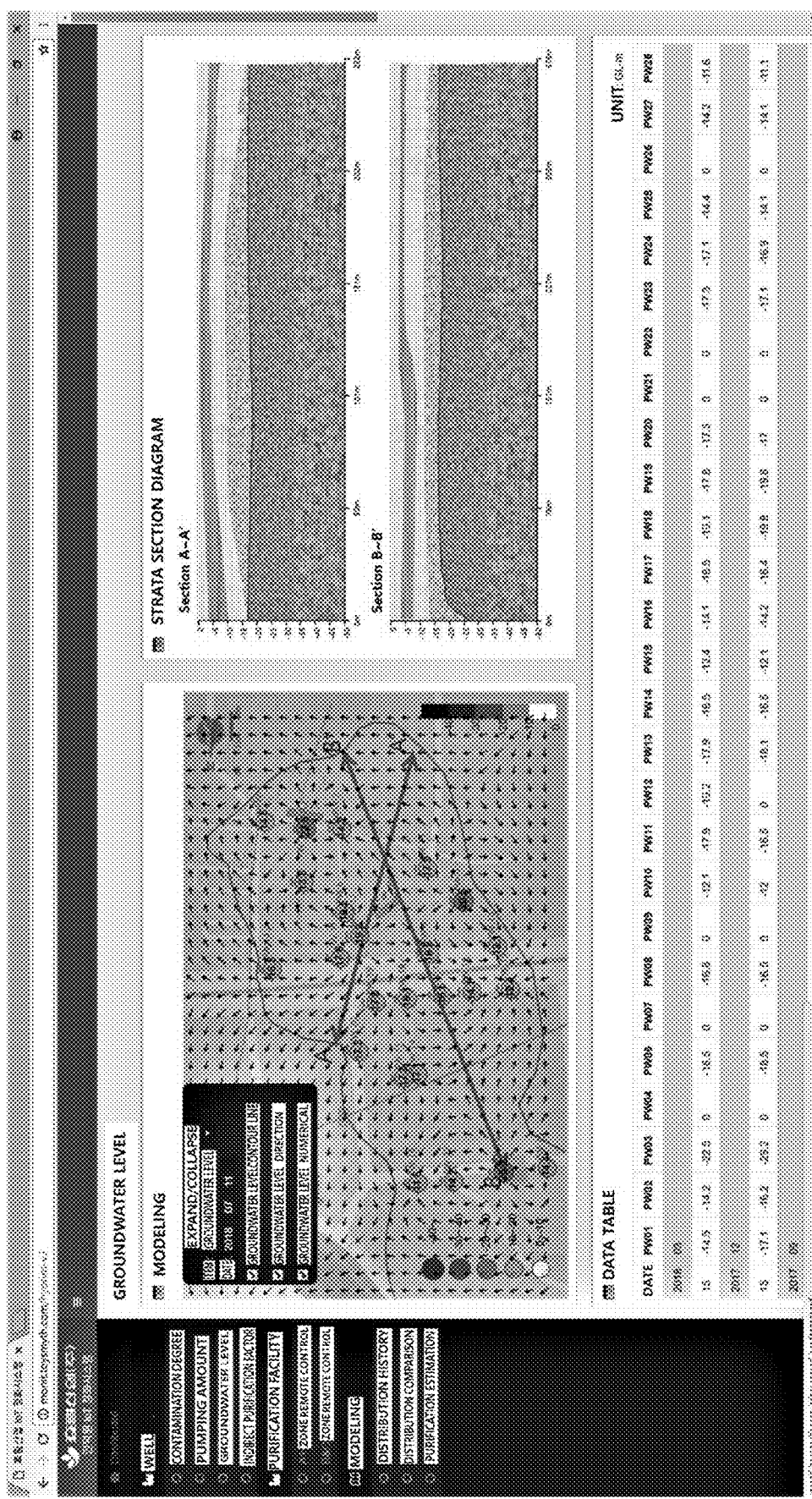
FIG. 9 is a groundwater level screen of the web dashboard unit of the IoT-based system for measurement of contamination distribution of contaminated groundwater through real-time monitoring of a contamination degree of a contaminated groundwater well for control of a contaminated groundwater purification device and prediction of a purification period based on the measurement result according to the present invention.

As shown in FIG. 9, the groundwater level screen includes a groundwater level modeling diagram, in which a groundwater level in each of the plurality of wells, a two-dimensional or three-dimensional potentiometric surface map of the groundwater level based thereon, and a groundwater flow direction diagram are displayed on the contaminated area map, a strata section diagram indicating the groundwater level displayed on the contaminated area map and the strata in a sectional manner, and a groundwater level data table indicating the groundwater level on a well basis and on a date basis.

Figure 10:
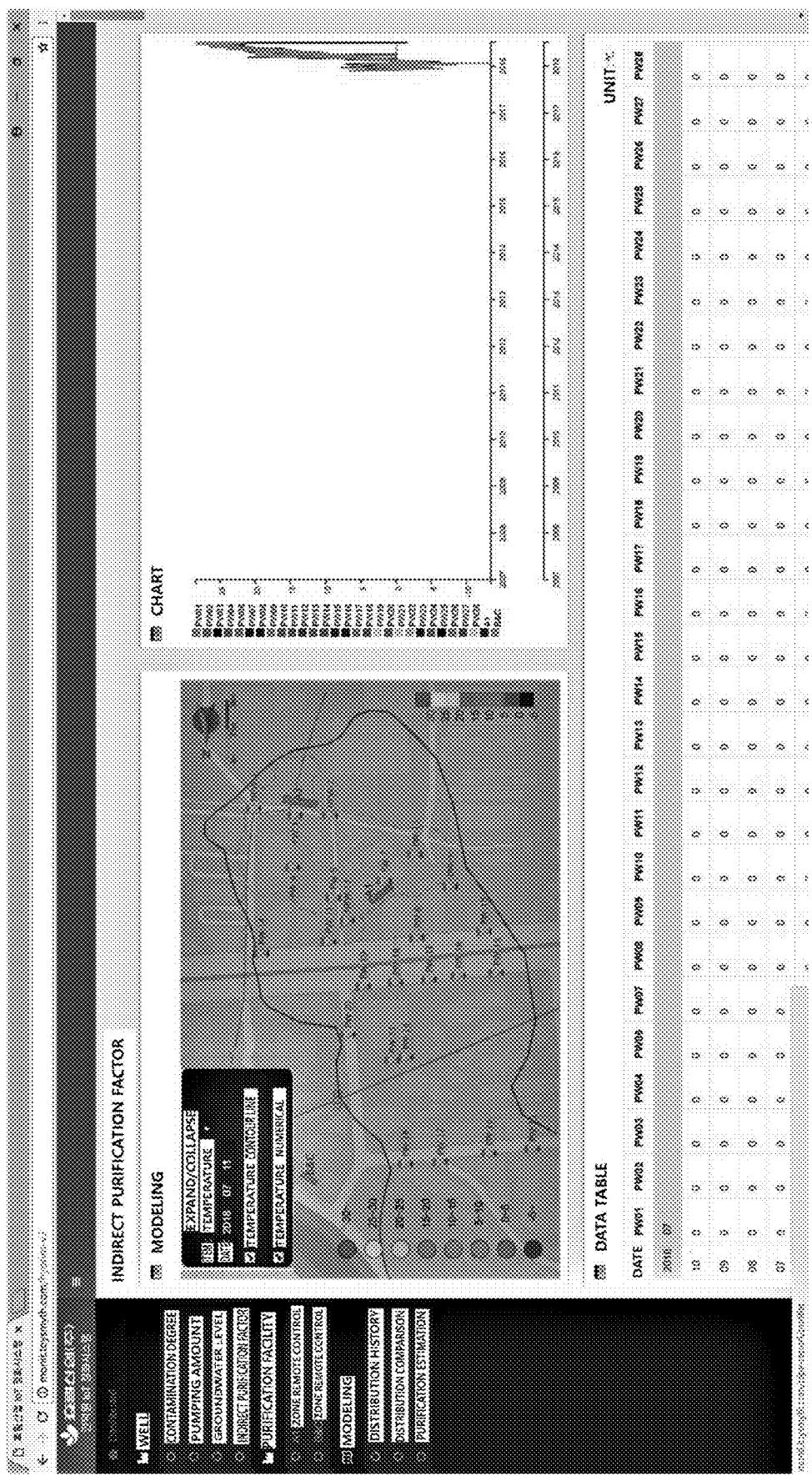
FIG. 10 is an indirect purification factor screen of the web dashboard unit of the IoT-based system for measurement of contamination distribution of contaminated groundwater through real-time monitoring of a contamination degree of a contaminated groundwater well for control of a contaminated groundwater purification device and prediction of a purification period based on the measurement result according to the present invention.
Figure 11:
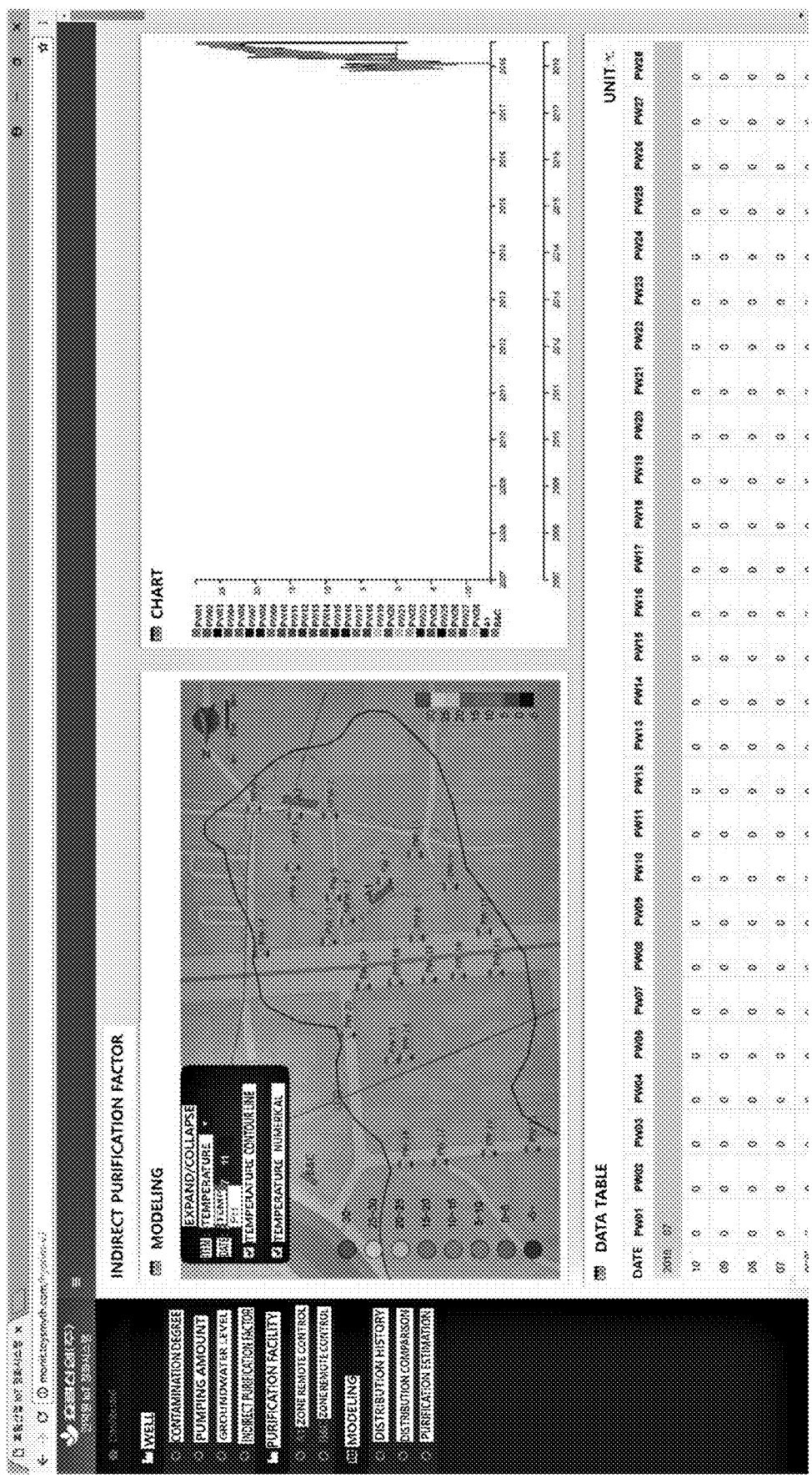
FIG. 11 is the indirect purification factor screen of the web dashboard unit of the IoT-based system for measurement of contamination distribution of contaminated groundwater through real-time monitoring of a contamination degree of a contaminated groundwater well for control of a contaminated groundwater purification device and prediction of a purification period based on the measurement result according to the present invention.

As shown in FIGS. 10 and 11, the indirect purification factor screen includes an indirect purification factor modeling diagram, in which values of indirect purification factors including temperature, pH, and rainfall in each of the plurality of wells and a two-dimensional or three-dimensional potentiometric surface map of the indirect purification factors based thereon are displayed on the contaminated area map, an indirect purification factor chart indicating a change in the values of the indirect purification factors in each of the plurality of wells, and an indirect purification factor data table indicating the values of the indirect purification factors on a well basis and on a date basis.

Figure 12:
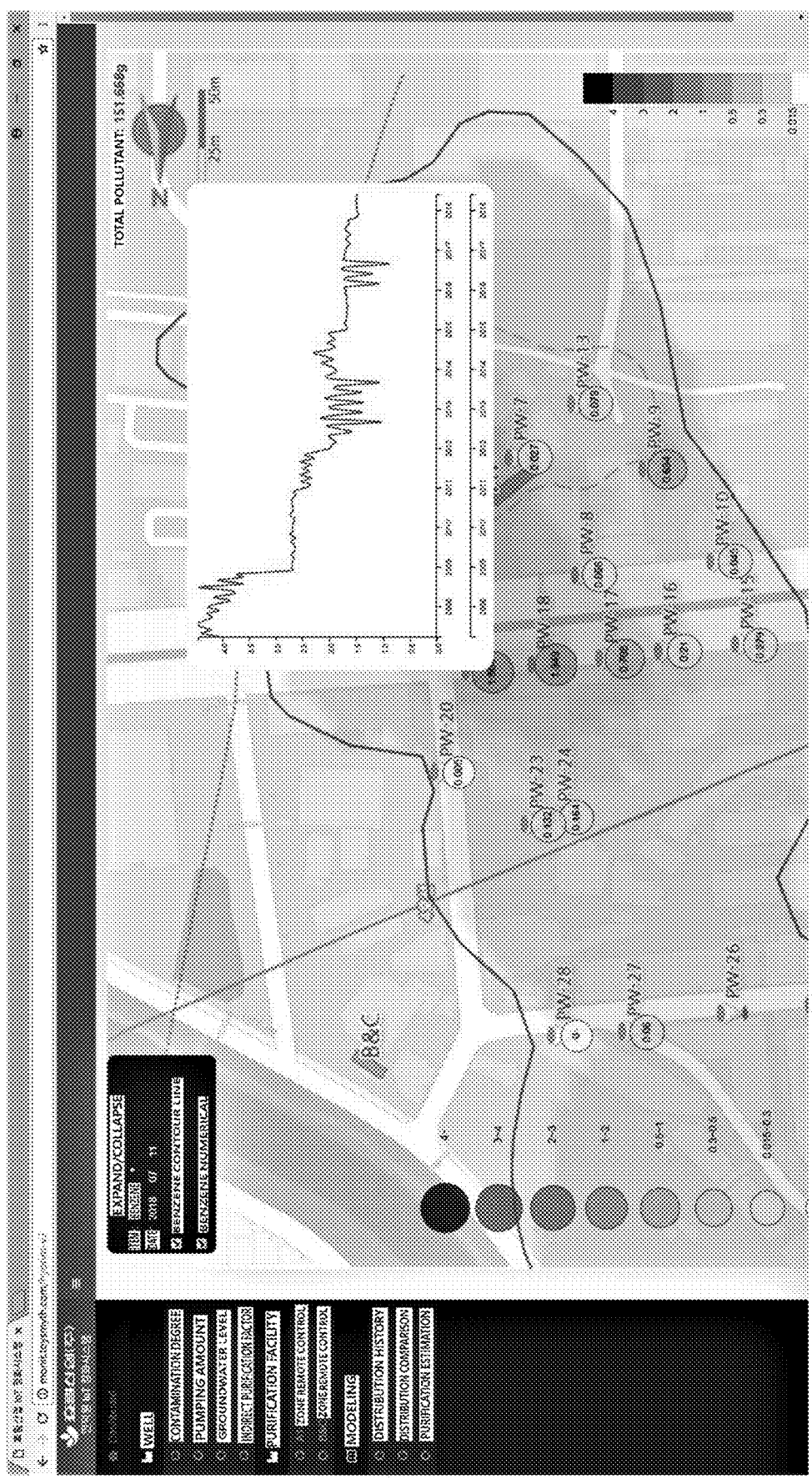
FIG. 12 is the main screen of the web dashboard unit of the IoT-based system for measurement of contamination distribution of contaminated groundwater through real-time monitoring of a contamination degree of a contaminated groundwater well for control of a contaminated groundwater purification device and prediction of a purification period based on the measurement result according to the present invention.

When each of the plurality of wells in the main screen is clicked and selected, the diameters and depths of the wells and the specifications of the pumps may be displayed on a well basis. In addition, as shown in FIG. 12, when each of the plurality of wells in the main screen is clicked and selected, a graph indicating a numerical change in each type of sensor data may be displayed.

In addition, although not illustrated, when the peak of the graph displayed in each of the contamination degree chart in the contamination degree screen, the pumping amount chart in the pumping amount screen, and the indirect purification factor chart in the indirect purification factor screen is clicked and selected, the degree of contamination of each contaminant, the pumping amount, and the value of each indirect purification factor on the corresponding date may be displayed.

Figure 13:
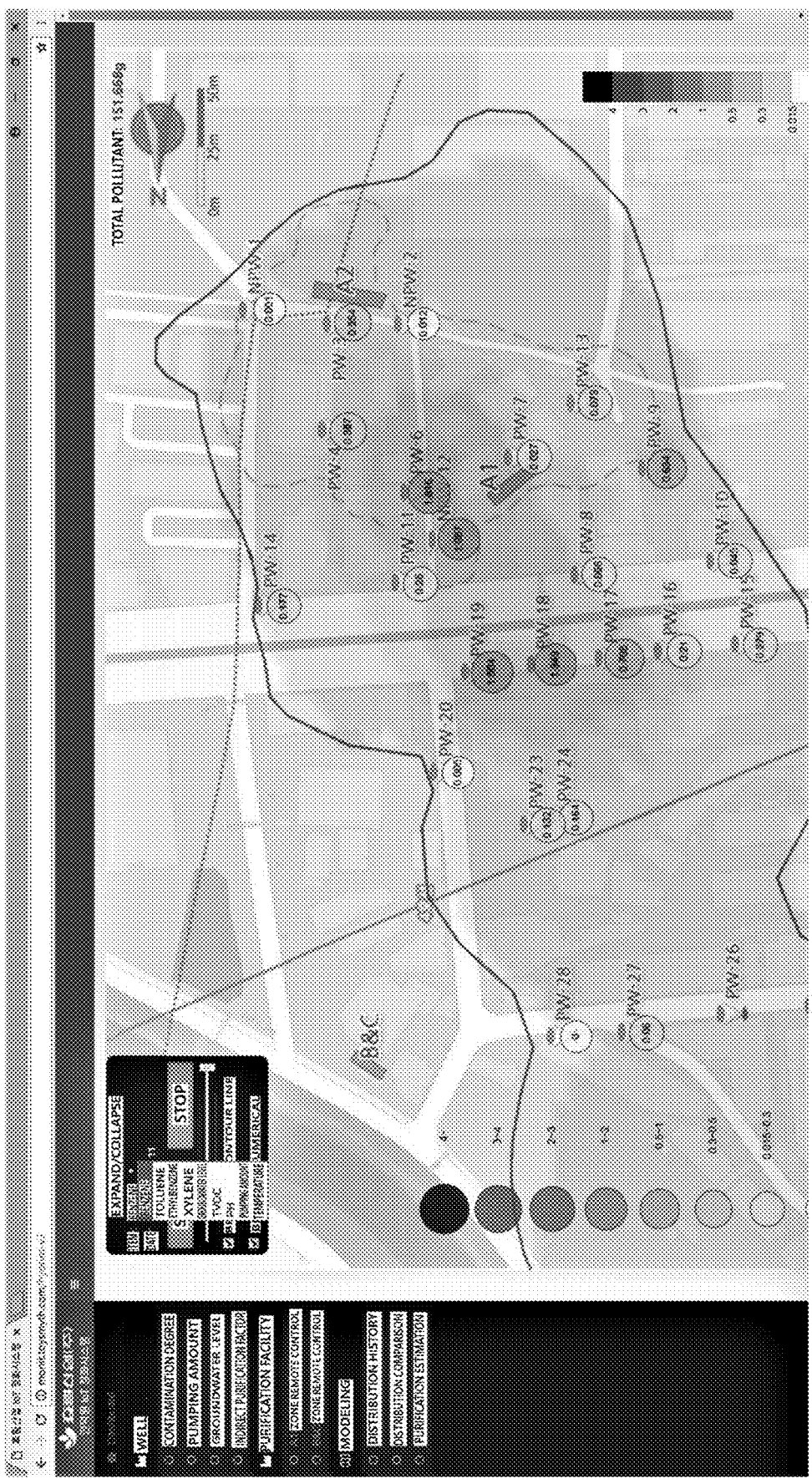
FIG. 13 is a distribution history screen of the web dashboard unit of the IoT-based system for measurement of contamination distribution of contaminated groundwater through real-time monitoring of a contamination degree of a contaminated groundwater well for control of a contaminated groundwater purification device and prediction of a purification period based on the measurement result according to the present invention.
Figure 14:
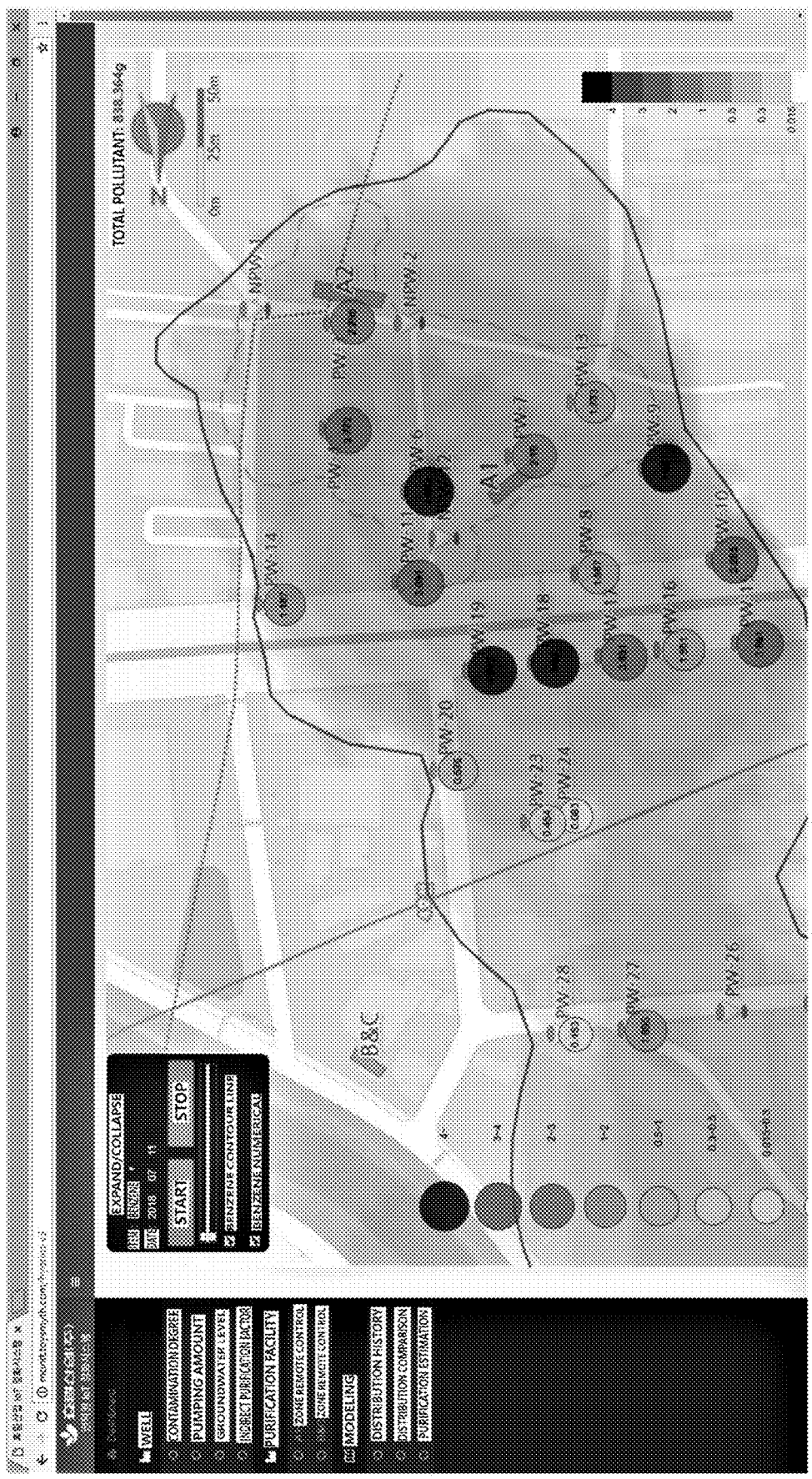
FIG. 14 is the distribution history screen of the web dashboard unit of the IoT-based system for measurement of contamination distribution of contaminated groundwater through real-time monitoring of a contamination degree of a contaminated groundwater well for control of a contaminated groundwater purification device and prediction of a purification period based on the measurement result according to the present invention.
Figure 15:
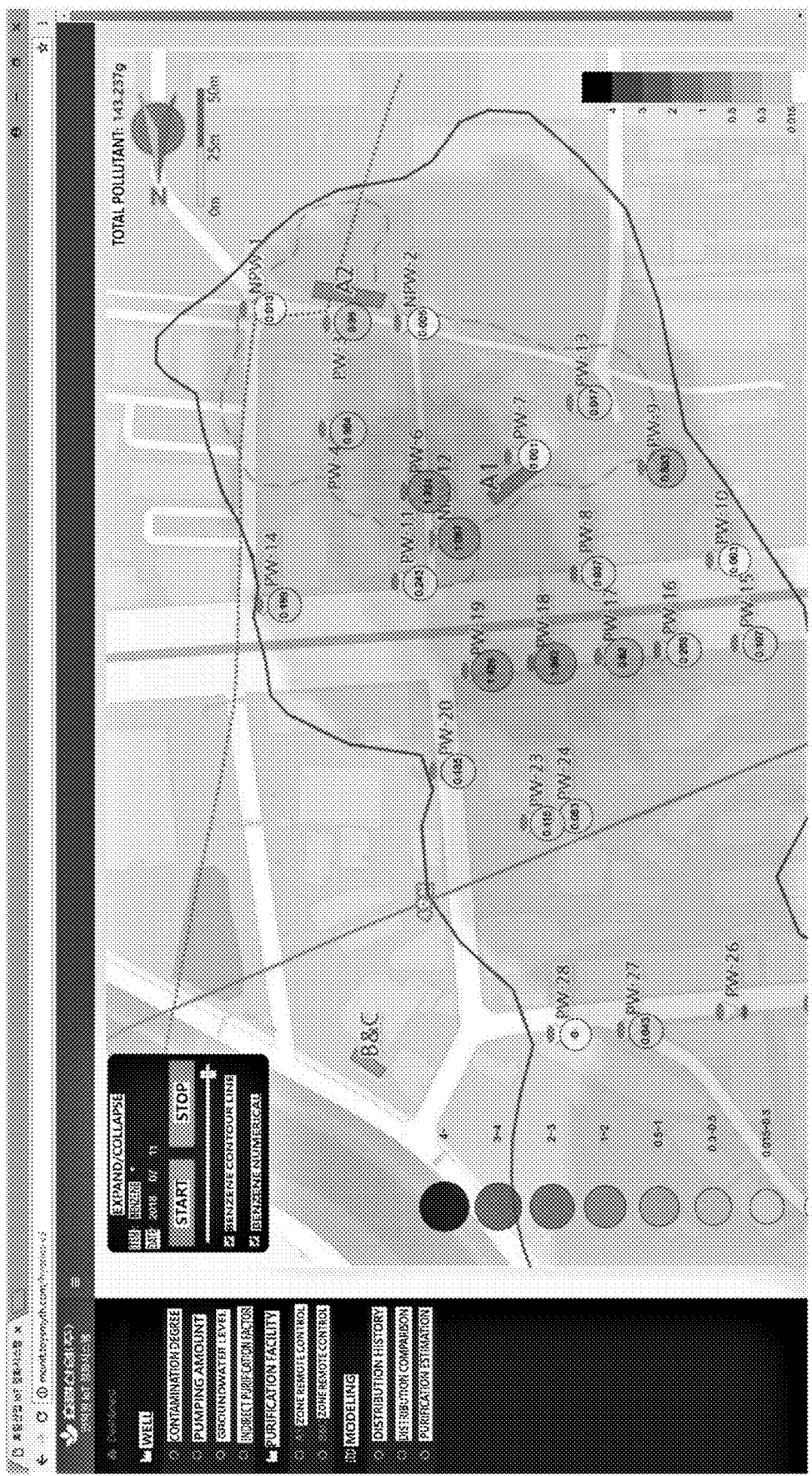
FIG. 15 is the distribution history screen of the web dashboard unit of the IoT-based system for measurement of contamination distribution of contaminated groundwater through real-time monitoring of a contamination degree of a contaminated groundwater well for control of a contaminated groundwater purification device and prediction of a purification period based on the measurement result according to the present invention.

As shown in FIGS. 13 to 15, the distribution history screen includes a sensor-data-type selection window enabling selection of the type of sensor data, the sensor-data-type selection window being displayed in a contamination map screen, in which a range of a contaminated area, a depth of contamination, a value of each type of sensor data on a well basis, a two-dimensional or three-dimensional potentiometric surface map based on the value of each type of sensor data, the location of the purification device, and the locations of the wells are displayed on a contaminated area map, further includes a period slide bar enabling selection of a start date and an end date, and displays a change history of the selected sensor data during a selected period, the change history of the selected sensor data including a range of a contaminated area, a depth of contamination, a value of each type of sensor data on a well basis, and a two-dimensional or three-dimensional potentiometric surface map based on the value of each type of sensor data.

That is, when a user or an administrator selects the type of sensor data in the distribution history screen and slides the period slide bar from a desired start point to a desired end point, a change history of the selected sensor data from the start date to the end date, which includes a range of a contaminated area, a depth of contamination, a value of each type of sensor data on a well basis, and a two-dimensional or three-dimensional potentiometric surface map based on the value of each type of sensor data, may be displayed, thereby making it possible to verify the contamination reduction state during the purification period.

Figure 16:
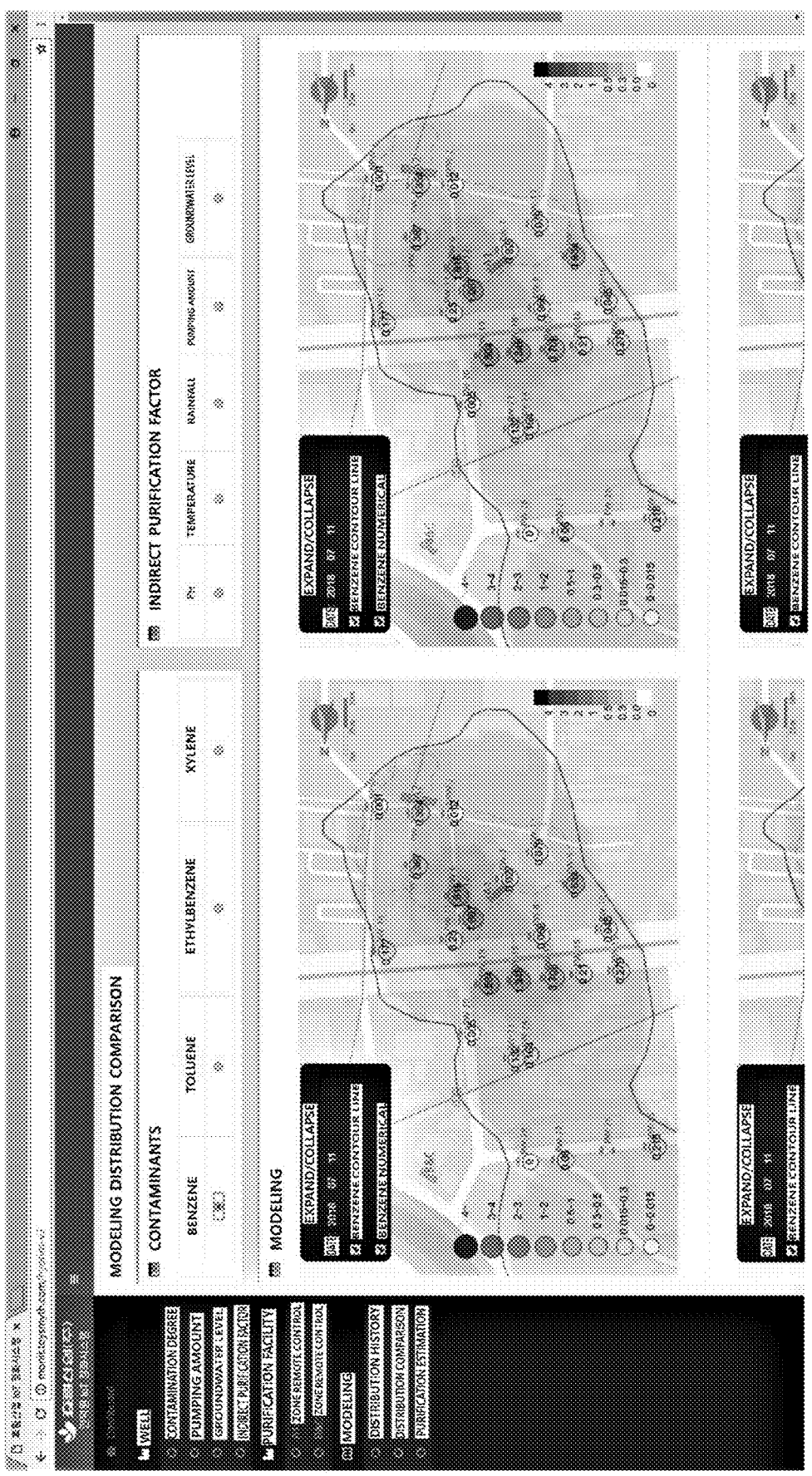
FIG. 16 is a distribution comparison screen of the web dashboard unit of the IoT-based system for measurement of contamination distribution of contaminated groundwater through real-time monitoring of a contamination degree of a contaminated groundwater well for control of a contaminated groundwater purification device and prediction of a purification period based on the measurement result according to the present invention.

As shown in FIG. 16, the distribution comparison screen includes a sensor-data-type selection window enabling selection of the type of sensor data and a plurality of comparison screens split on a period basis, in each of which a change history of the selected sensor data, which includes a range of a contaminated area, a depth of contamination, a value of each type of sensor data on a well basis, and a two-dimensional or three-dimensional potentiometric surface map based on the value of each type of sensor data, is displayed on a contaminated area map, thereby making it possible to verify the contamination reduction state during the purification period in a split manner.

In addition, the web dashboard of the present invention includes the purification control screen, which includes a sensor-data-type selection window enabling selection of the type of sensor data, the sensor-data-type selection window being displayed in a contamination map screen, in which a range of a contaminated area, a depth of contamination, a value of each type of sensor data on a well basis, a two-dimensional or three-dimensional potentiometric surface map based on the value of each type of sensor data, the location of the purification device, the locations of the wells, and connection pipes are displayed on a contaminated area map.

Figure 17:
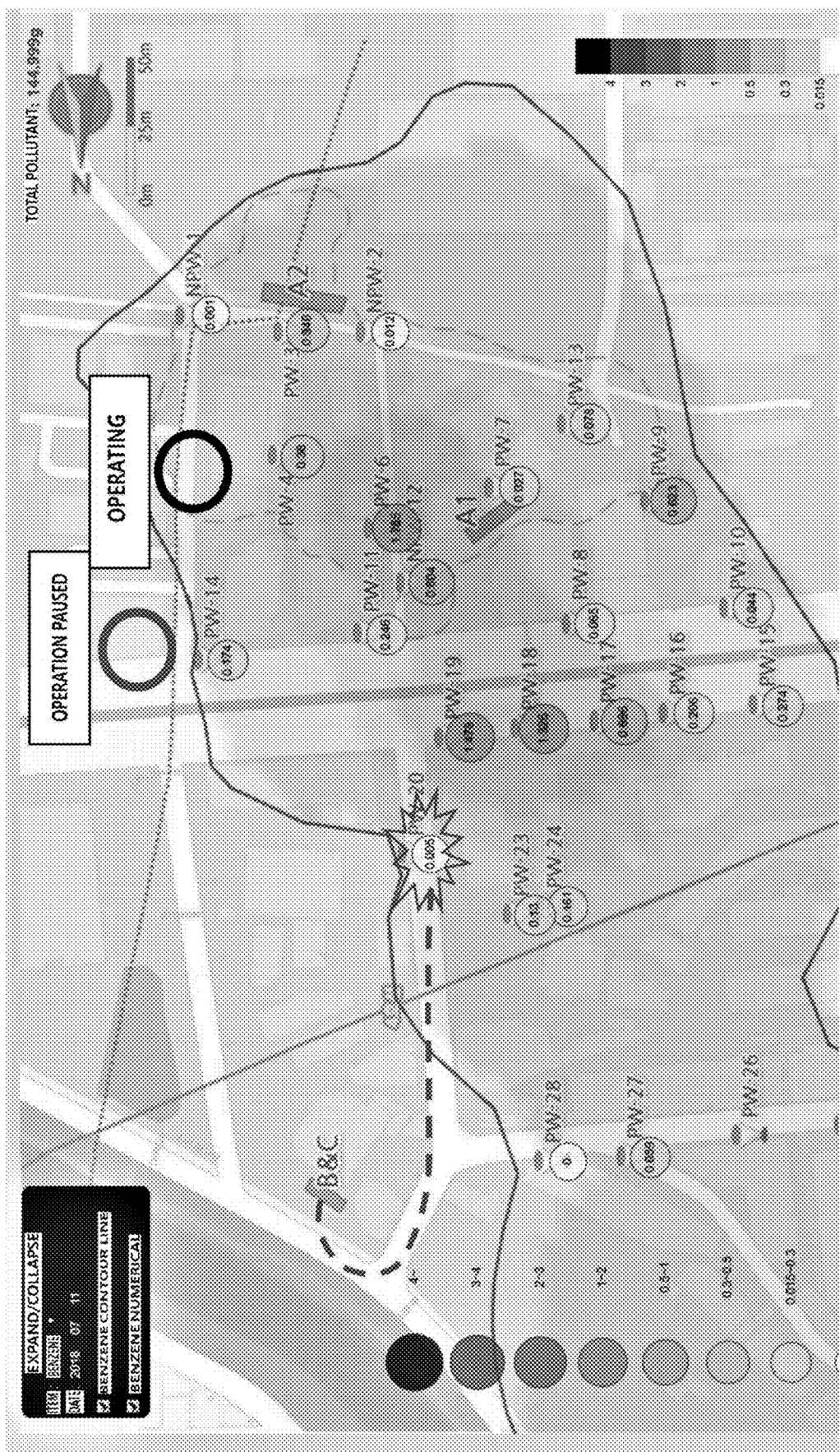
FIG. 17 is a purification control screen of the web dashboard unit of the IoT-based system for measurement of contamination distribution of contaminated groundwater through real-time monitoring of a contamination degree of a contaminated groundwater well for control of a contaminated groundwater purification device and prediction of a purification period based on the measurement result according to the present invention.

That is, as shown in FIG. 17, the purification control screen includes a contamination map screen, in which a range of a contaminated area, a depth of contamination, a value of each type of sensor data on a well basis, a two-dimensional or three-dimensional potentiometric surface map based on the value of each type of sensor data, the location of the purification device, the locations of the wells, and connection pipes are displayed on a contaminated area map.

Figure 18:
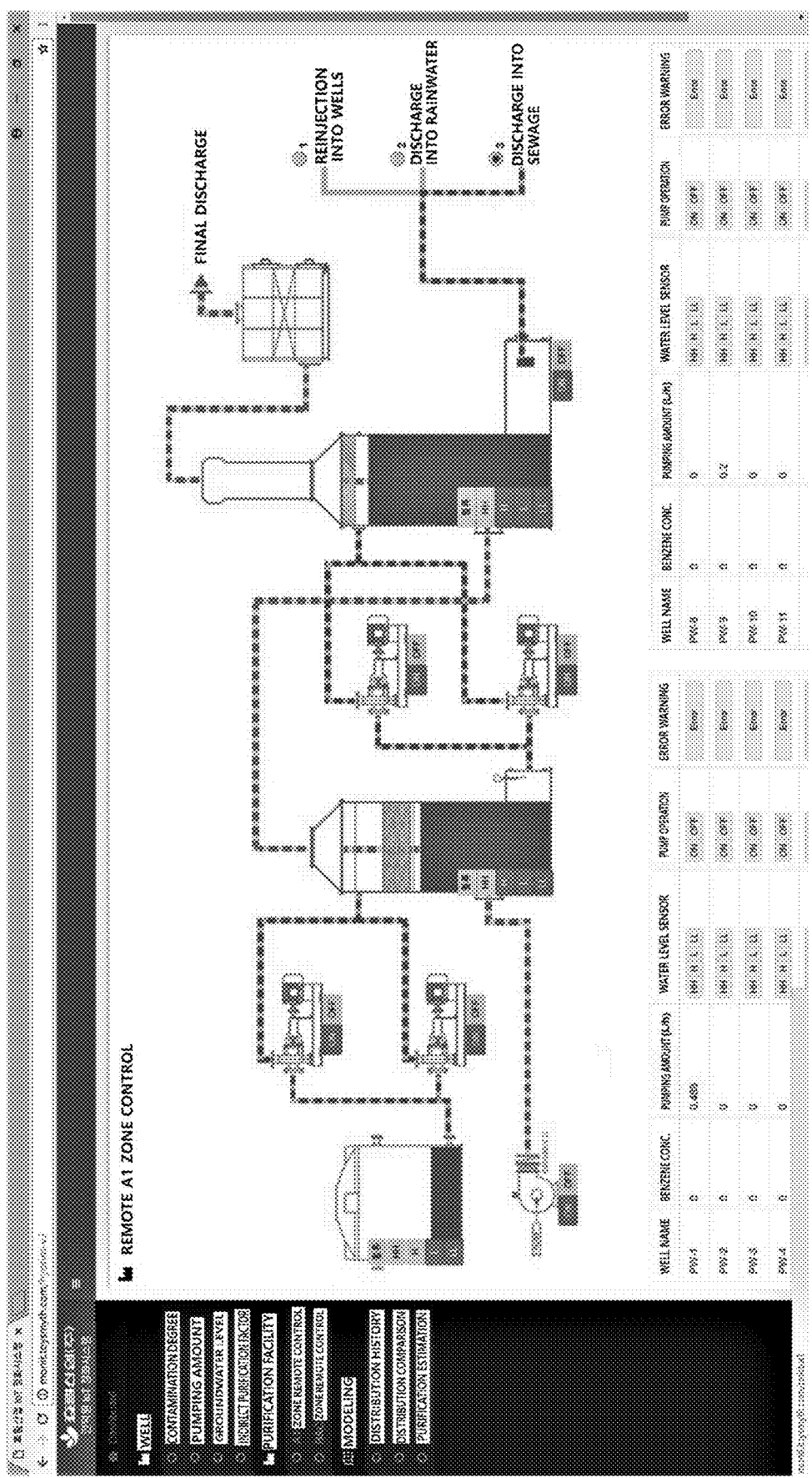
FIG. 18 is a purification device operation screen of the web dashboard unit of the IoT-based system for measurement of contamination distribution of contaminated groundwater through real-time monitoring of a contamination degree of a contaminated groundwater well for control of a contaminated groundwater purification device and prediction of a purification period based on the measurement result according to the present invention.

When a purification device in the contamination map screen is clicked and selected, as shown in FIG. 18, a purification device operation screen is displayed. The purification device operation screen includes an entire construction diagram of the purification device in each purification zone, a flow indicator indicating the flow of contaminated groundwater through the pipes of the purification device, reinjection into the wells, discharge into rainwater, and discharge into sewage, and an operation data table indicating the degree of contamination by the contaminants in each well, an amount pumped from each well, a water level in each well, a water level in the purification device, on/off of a pump in each well, on/off of a pump of the purification device, on/off of a pump supplying a chemical, and information about whether the purification device is operating normally.

In addition, the purification device operation screen may display a chart indicating the name of an injected chemical, the amount of the chemical that is injected, and a numerical change in the amount of the chemical that is injected.

In addition, on/off of the pump in each well, on/off of the pump of the purification device, and on/off of the pump supplying a chemical may be respectively controlled through the purification device operation screen.

Figure 19:
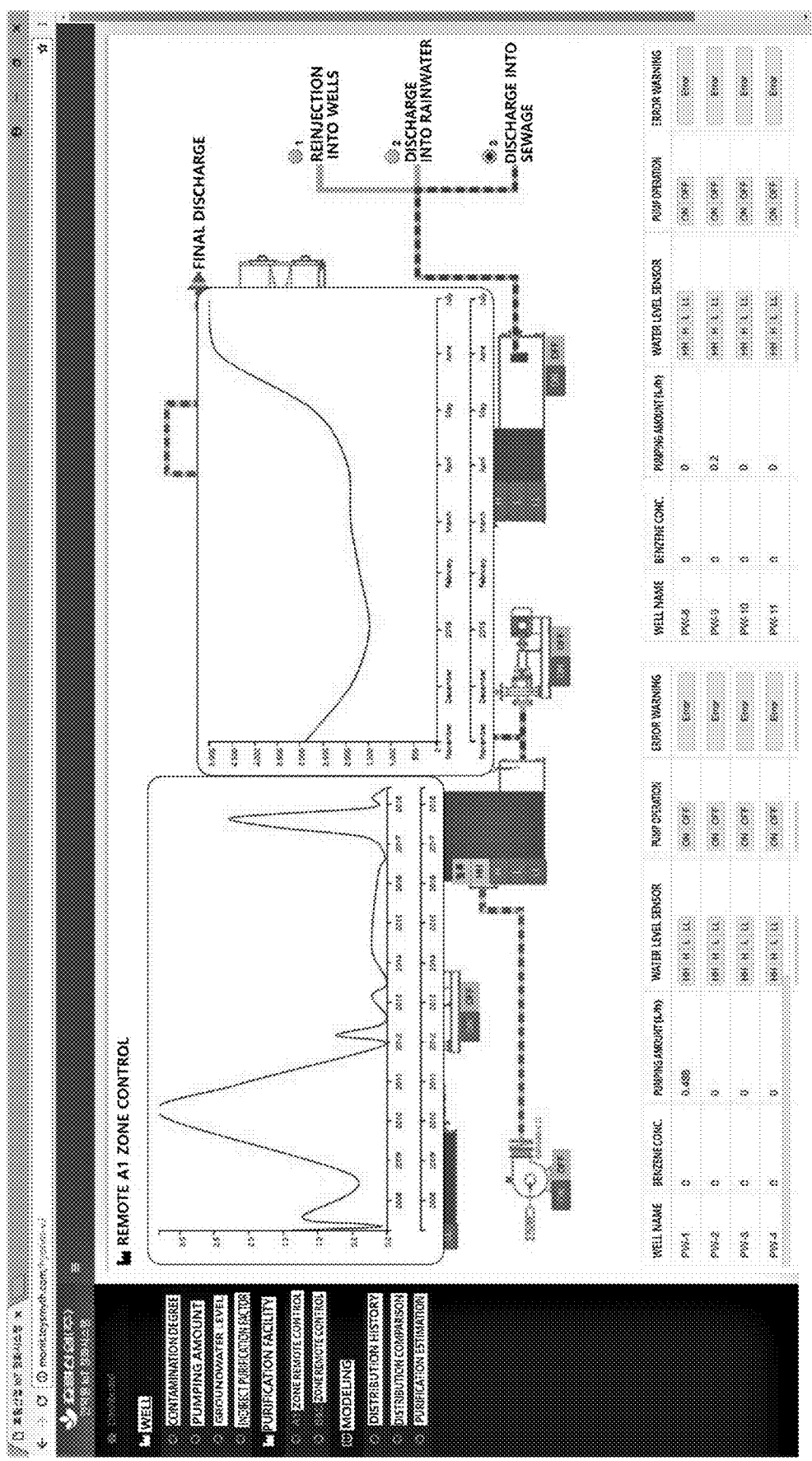
FIG. 19 is the purification device operation screen of the web dashboard unit of the IoT-based system for measurement of contamination distribution of contaminated groundwater through real-time monitoring of a contamination degree of a contaminated groundwater well for control of a contaminated groundwater purification device and prediction of a purification period based on the measurement result according to the present invention.
Figure 20:
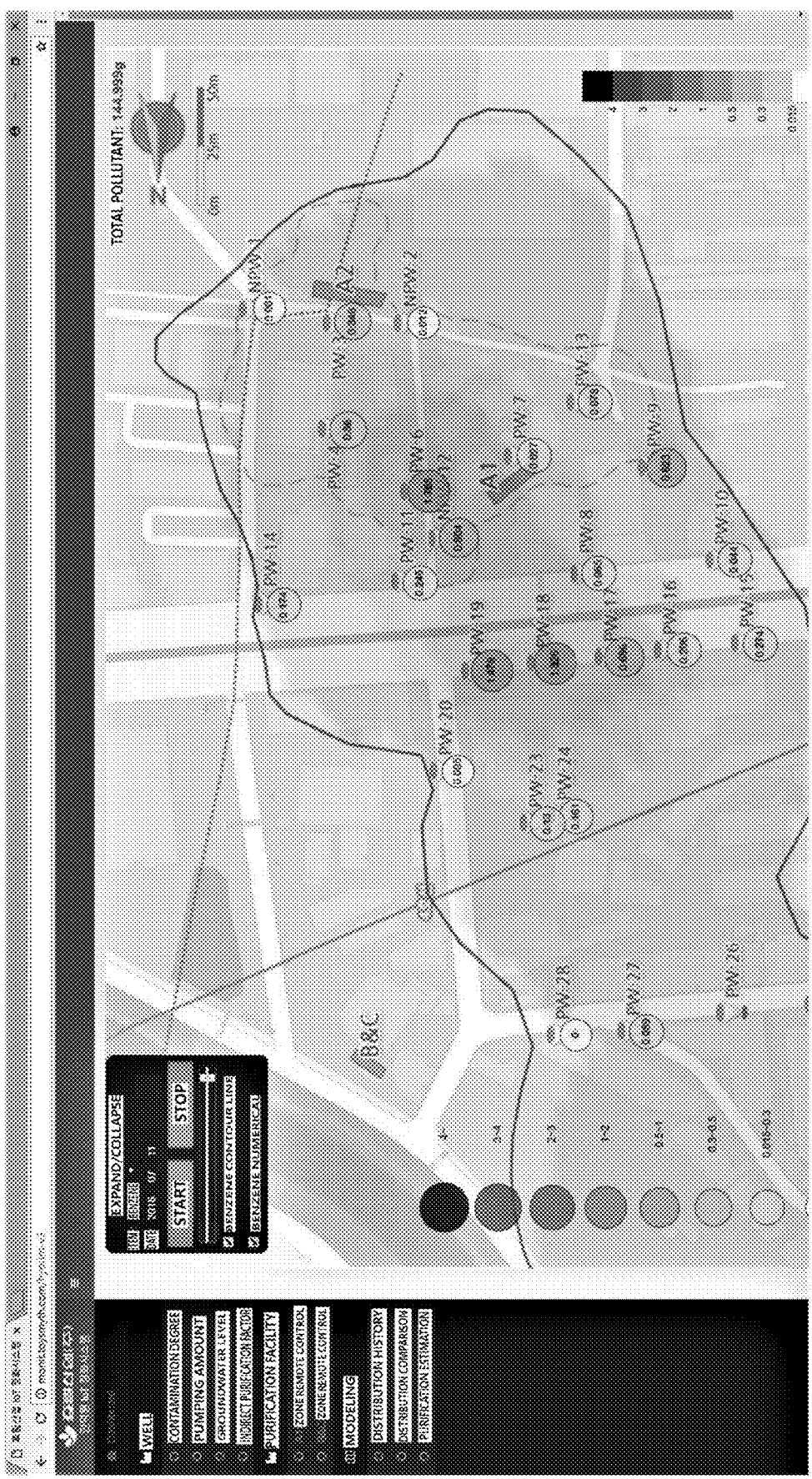
FIG. 20 is a purification period prediction screen of the web dashboard unit of the IoT-based system for measurement of contamination distribution of contaminated groundwater through real-time monitoring of a contamination degree of a contaminated groundwater well for control of a contaminated groundwater purification device and prediction of a purification period based on the measurement result according to the present invention.
Figure 21:
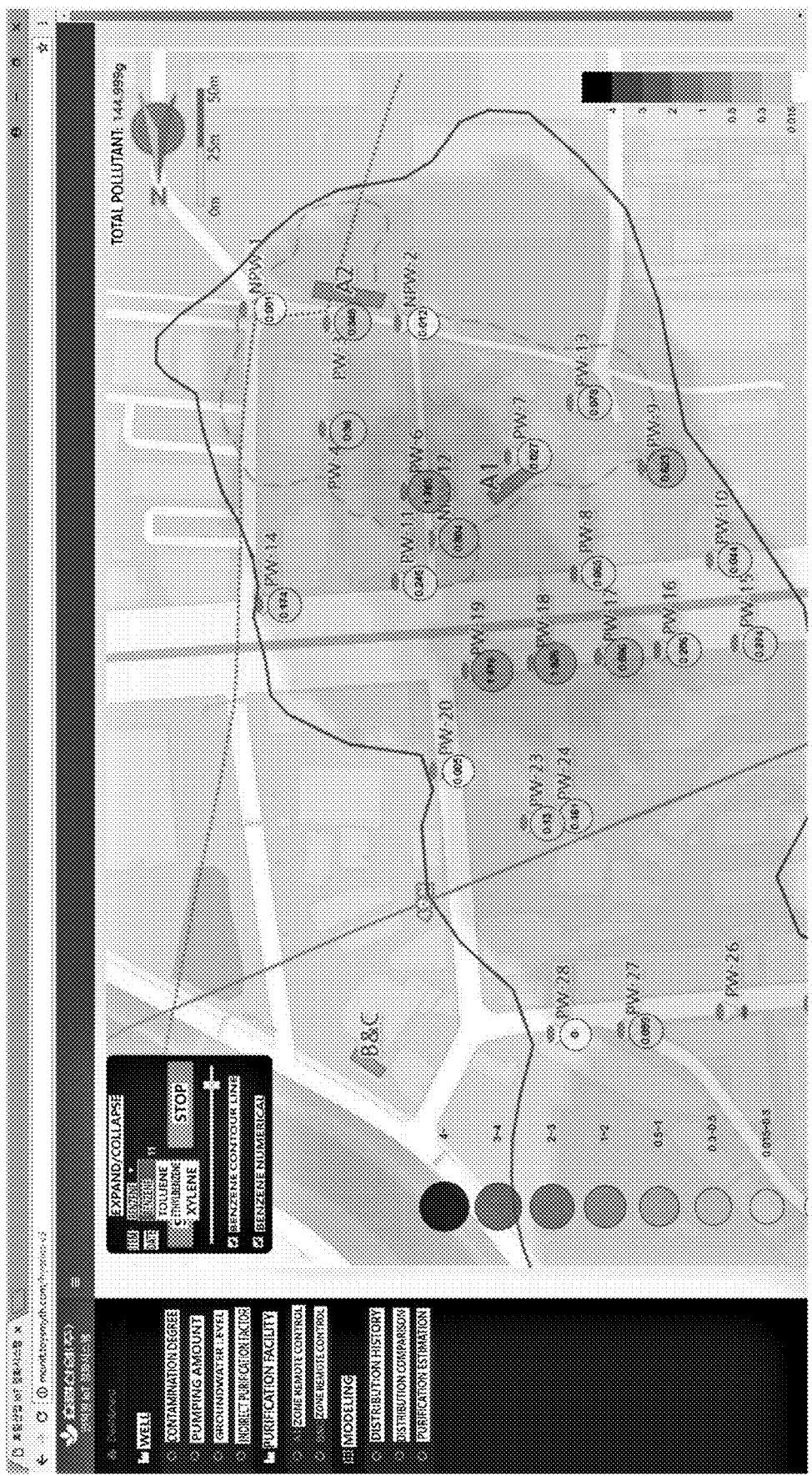
FIG. 21 is the purification period prediction screen of the web dashboard unit of the IoT-based system for measurement of contamination distribution of contaminated groundwater through real-time monitoring of a contamination degree of a contaminated groundwater well for control of a contaminated groundwater purification device and prediction of a purification period based on the measurement result according to the present invention.
Figure 22:
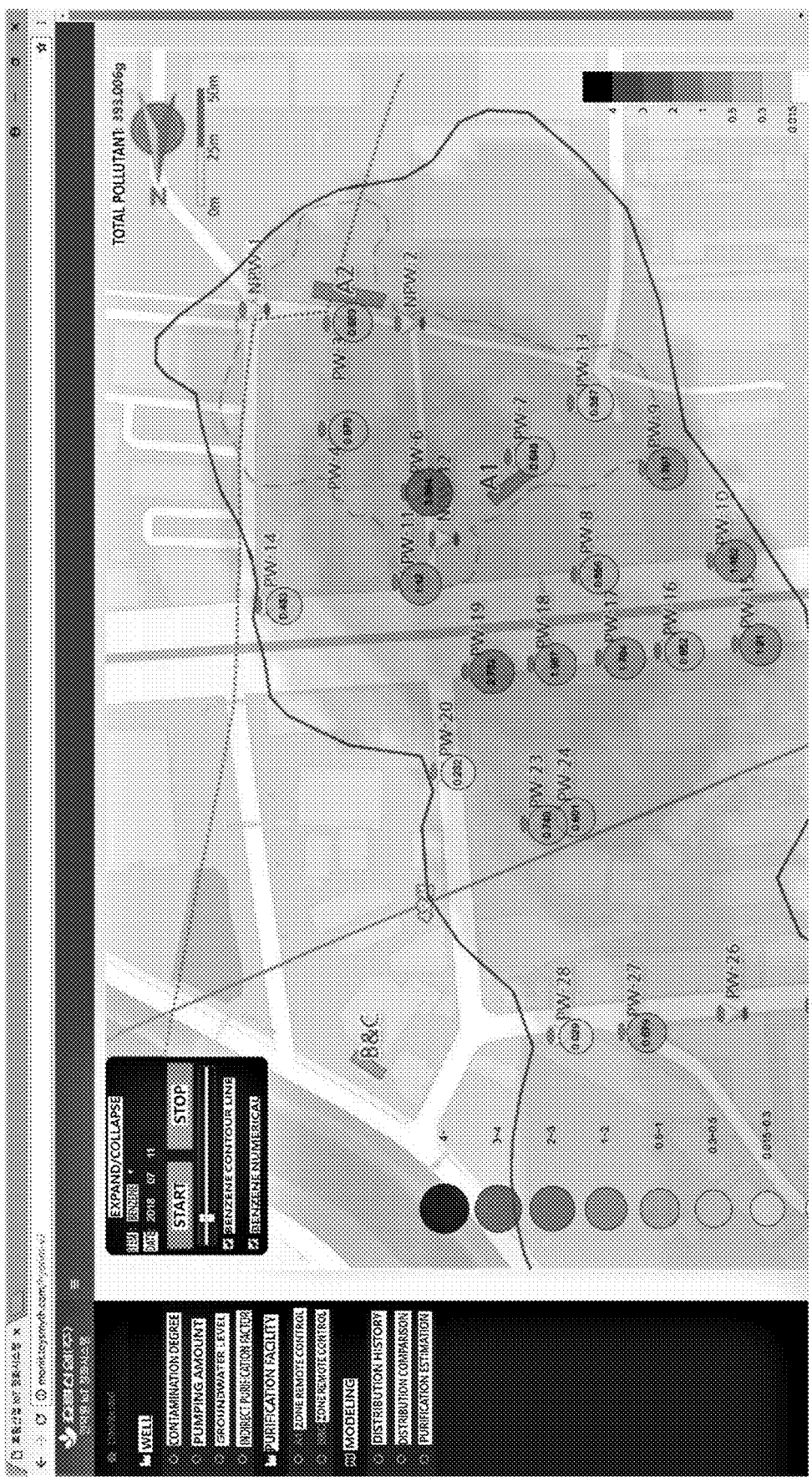
FIG. 22 is the purification period prediction screen of the web dashboard unit of the IoT-based system for measurement of contamination distribution of contaminated groundwater through real-time monitoring of a contamination degree of a contaminated groundwater well for control of a contaminated groundwater purification device and prediction of a purification period based on the measurement result according to the present invention.
Figure 23:
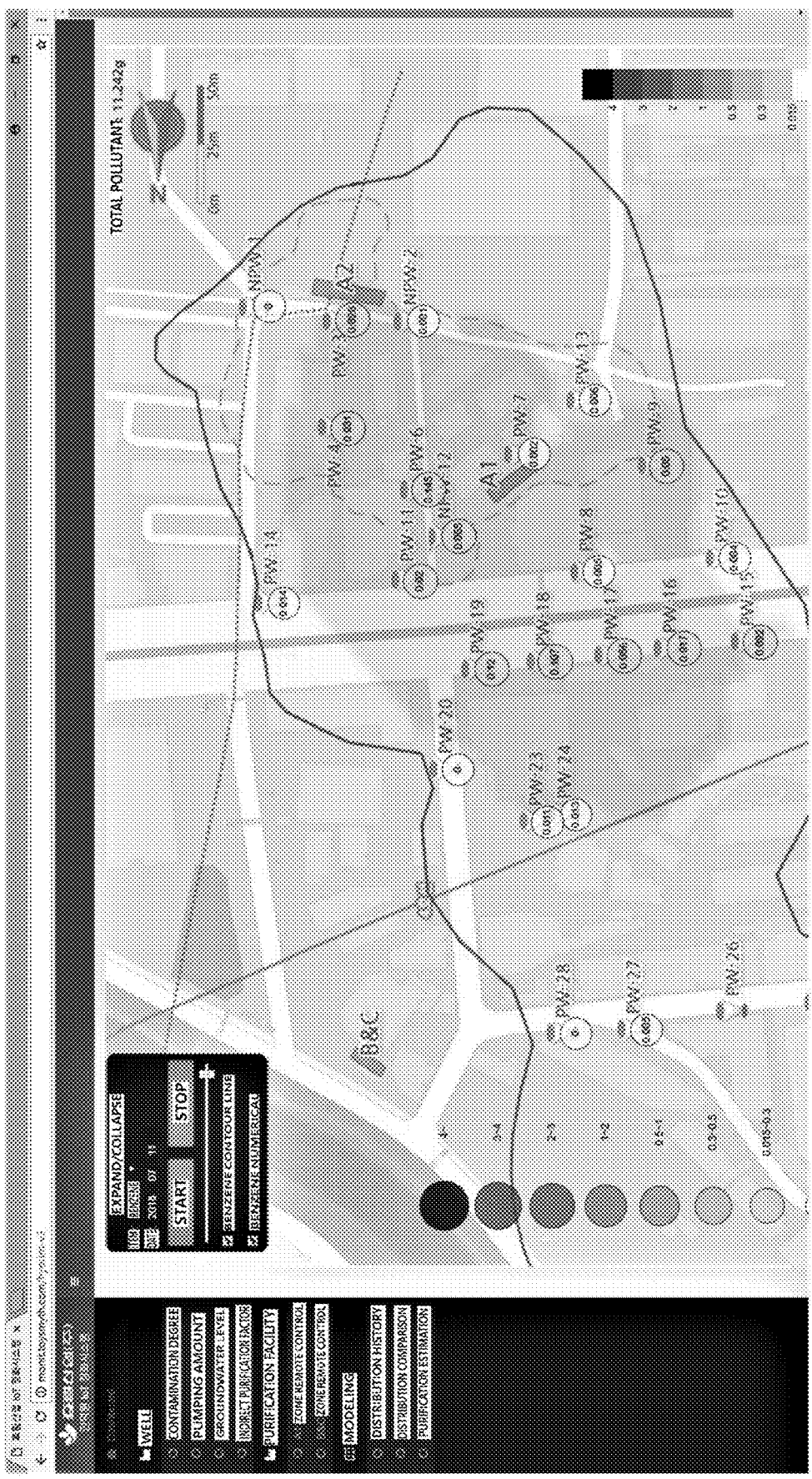
FIG. 23 is the purification period prediction screen of the web dashboard unit of the IoT-based system for measurement of contamination distribution of contaminated groundwater through real-time monitoring of a contamination degree of a contaminated groundwater well for control of a contaminated groundwater purification device and prediction of a purification period based on the measurement result according to the present invention.

In addition, as shown in FIG. 19, when an inlet tank and an outlet tank of the purification device displayed in the purification device operation screen are respectively clicked and selected, a graph indicating a numerical change in the degree of contamination by the contaminants may be displayed.

Meanwhile, the web dashboard of the present invention includes the purification period prediction screen displaying a change in the value of each type of sensor data in the contaminated area.

That is, as shown in FIGS. 20 to 23, the purification period prediction screen includes a sensor-data-type selection window enabling selection of the type of sensor data, the sensor-data-type selection window being displayed in a contamination map screen, in which a range of a contaminated area, a depth of contamination, a value of each type of sensor data on a well basis, a two-dimensional or three-dimensional potentiometric surface map based on the value of each type of sensor data, the location of the purification device, and the locations of the wells are displayed on a contaminated area map, further includes a period slide bar enabling selection of a start date and an end date, and displays a change history of the selected sensor data during a selected period, the change history of the selected sensor data including a range of a contaminated area, a depth of contamination, a value of each type of sensor data on a well basis, and a two-dimensional or three-dimensional potentiometric surface map based on the value of each type of sensor data.

The purification period prediction screen is configured to enable verification of a contamination reduction state during the selected period based on the change history during the selected period.

That is, when a user or an administrator selects the type of sensor data in the purification period prediction screen and slides the period slide bar from a desired start point to a desired end point, a change history of the selected sensor data from the start date to the end date, which includes a range of a contaminated area, a depth of contamination, a value of each type of sensor data on a well basis, and a two-dimensional or three-dimensional potentiometric surface map based on the value of each type of sensor data, may be displayed, thereby making it possible to verify the contamination reduction state during the purification period.

Figure 24:
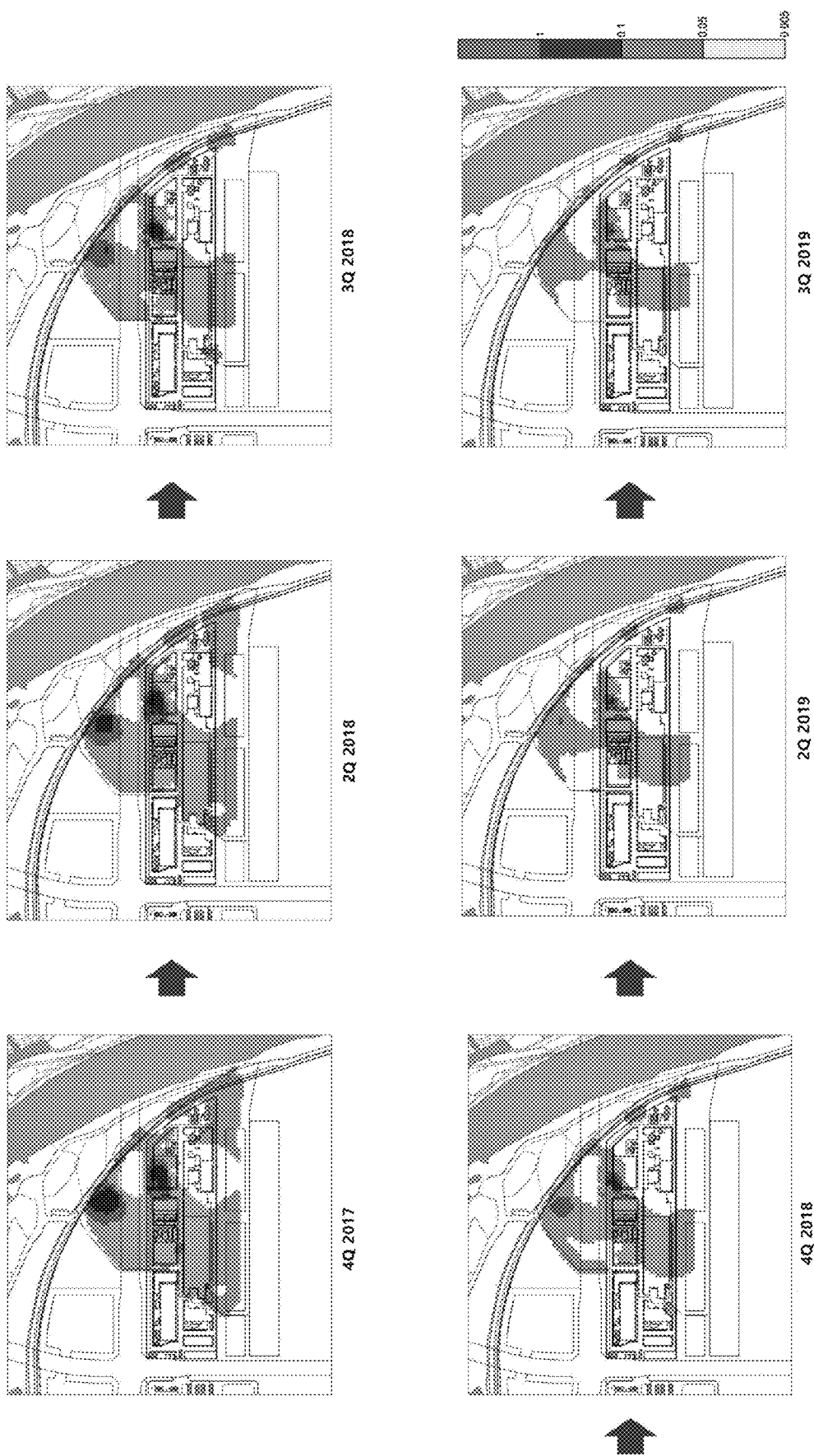
FIG. 24 is the purification period prediction screen of the web dashboard unit of the IoT-based system for measurement of contamination distribution of contaminated groundwater through real-time monitoring of a contamination degree of a contaminated groundwater well for control of a contaminated groundwater purification device and prediction of a purification period based on the measurement result according to the present invention

For example, as shown in FIG. 24, based on the change history of the two-dimensional or three-dimensional potentiometric surface map over time, which is displayed in the purification period prediction screen, it is possible to verify the contamination reduction state during the purification period and consequently to predict the total purification period required for complete purification.

Meanwhile, the purification period prediction screen is configured to output a predicted value of the degree of contamination after a predetermined period and a predicted value of the purification period. The predicted value of the degree of contamination after a predetermined period and the predicted value of the purification period are calculated using a program executed based on a purification period prediction algorithm including the exponential function below:

$$C=C_0 e^{-kt}$$

where C indicates the degree of contamination (mg/L) of groundwater after a predetermined period, C0 indicates the initial degree of contamination (mg/L) of groundwater, k indicates the reduction coefficient ($day^{-1}$), and t indicates the time (day).

In this case, the predicted value of the degree of contamination after a predetermined period is calculated such that the reduction coefficient k ($day^{-1}$) is calculated from the degree of contamination C (mg/L) of groundwater after a predetermined period (day) and the initial degree of contamination $C_0$ (mg/L) of groundwater, among the sensor data of the contamination degree sensor, a graph of the aforementioned exponential function is output, and the predicted value of the degree of contamination after a predetermined period (day) is calculated using the graph.

In addition, the predicted value of the purification period is calculated such that the reduction coefficient k ($day^{-1}$) is calculated from the degree of contamination C (mg/L) of groundwater after a predetermined period (day) and the initial degree of contamination $C_0$ (mg/L) of groundwater, among the sensor data of the contamination degree sensor, a graph of the aforementioned exponential function is output, a contamination purification target is set using the graph, and a period within which it is required to accomplish the contamination purification target is calculated as the predicted value of the purification period.

In addition, the purification period prediction screen may display the amount of the chemical that is injected and the amount of power that is consumed during a selected period, and may calculate and display a predicted value of the amount of the chemical to be injected and a predicted value of the amount of power to be consumed during the period corresponding to the predicted value of the purification period using the program to which the purification period prediction algorithm is applied based on the amount of the chemical that is injected and the amount of power that is consumed.

In addition, a two-dimensional or three-dimensional potentiometric surface map of the sensor data, a two-dimensional or three-dimensional potentiometric surface map of each contaminant, a two-dimensional or three-dimensional potentiometric surface map of the pumping amount, a two-dimensional or three-dimensional potentiometric surface map of the groundwater level, or a two-dimensional or three-dimensional potentiometric surface map of each indirect purification factor displayed in the web dashboard screen of the present invention is configured to indicate numerical ranges such that the numerical ranges are distinguished by colors.

In addition, the IoT-based system for measurement of contamination distribution of contaminated groundwater through real-time monitoring of a contamination degree of a contaminated groundwater well for control of a contaminated groundwater purification device and prediction of a purification period based on the measurement result according to the present invention may be configured to allow a purification company or a supervisory institution to have online access thereto so as to perform verification or control.

As is apparent from the above description, the present invention provides an IoT-based system for measurement of contamination distribution of contaminated groundwater through real-time monitoring of a contamination degree of a contaminated groundwater well for control of a contaminated groundwater purification device and prediction of a purification period based on the measurement result, which monitors a groundwater well in real time based on sensor data collected from the contaminated groundwater well in the process of purifying contaminated groundwater present under the ground, measures the contamination distribution of the contaminated groundwater based on the monitoring result, controls a contaminated groundwater purification device, and predicts a purification period based on the measurement result, thereby efficiently purifying the contaminated groundwater. Thus, it is possible to monitor a degree of contamination of groundwater in real time without the necessity to investigate the degree of contamination of groundwater through multiple separate methods, thereby reducing the amount of labor, time, and expense required to investigate the degree of contamination. In addition, it is possible to accomplish automated purification by automatically controlling the purification device based on the contamination distribution of contaminated groundwater. In addition, it is possible to predict the degree of contamination after a predetermined period of time or to predict the total purification period required to accomplish the target degree of contamination to be purified, thereby realizing efficient purification treatment.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An IoT-based system for measurement of contamination distribution of contaminated groundwater through real-time monitoring of a contamination degree of a contaminated groundwater well for prediction of a purification period based on a measurement result, the IoT-based system comprising:

a sensor unit mounted in each of a plurality of wells excavated to purify contaminated groundwater, the sensor unit comprising a contamination degree sensor for measuring a degree of contamination by contaminants, a pH sensor, a temperature sensor, a water level sensor, a pumping amount sensor, and a rainfall sensor;

a server unit configured to collect sensor data transmitted from the sensor unit and to classify the sensor data based on a data type; and a web dashboard unit configured to display the sensor data transmitted from the server unit to enable a user to verify or control desired sensor data on a well basis and on a data-type basis in real time, the web dashboard unit comprising a purification-area-based status screen, a main screen, a contamination degree screen, a pumping amount screen, a groundwater level screen, an indirect purification factor screen, a contaminated-area-sensor-data-based movement distribution history screen, a distribution comparison screen, a purification control screen comprising a sensor-data-type selection window enabling selection of a type of sensor data, the sensor-data-type selection window being displayed in a contamination map screen, in which a range of a contaminated area, a depth of contamination, a value of each type of sensor data on a well basis, a two-dimensional or three-dimensional potentiometric surface map based on the value of each type of sensor data, a location of a purification device, locations of the wells, and connection pipes are displayed on a contaminated area map, and a purification period prediction screen displaying a change in the value of each type of sensor data in a contaminated area, wherein the contaminated groundwater is purified such that the contaminated groundwater is pumped from the plurality of wells and is purified on a ground by the purification device or such that a purification agent is injected into each of the plurality of wells and the contaminated groundwater mixed with the purification agent is pumped and purified by the purification device, wherein the contaminants comprise: petroleum-based contaminants comprising benzene, toluene, xylene, ethyl benzene, total petroleum hydrocarbon (TPH), trichloroethylene (TCE), tetrachloroethylene (PCE), organophosphorus compound, PCB, cyan, and phenol; and heavy metal contaminants comprising arsenic, lead, cadmium, hexavalent chromium, copper, mercury, zinc, nickel, and fluorine, wherein the contamination degree sensor is selectively implemented, depending on the contaminants, as any of analysis devices comprising a gas chromatograph (GC), a gas chromatography-mass spectrometer (GC-MS), an atomic absorption spectrophotometer, an atomic emission spectrophotometer, an absorption spectrophotometer, an infrared spectrophotometer, and an ultraviolet spectrophotometer, wherein the contamination degree sensor measures a degree of contamination using contaminated groundwater sampled from the wells, wherein the purification-area-based status screen comprises: a status screen configured to display a construction project name, a construction period, types of contaminants, a cause of contamination, a purification standard, and a purification promotion history; and a contamination map screen, in which a range of a contaminated area, a depth of contamination, a location of the purification device, locations of the wells, and connection pipes are displayed on a contaminated area map, wherein the main screen comprises a sensor-data-type selection window enabling selection of a type of sensor data, and displays a value of each type of sensor data selected from each of the plurality of wells and a two-dimensional or three-dimensional potentiometric surface map based on the value of each type of sensor data on a contaminated area map, wherein the contamination degree screen comprises: a contaminant-type selection window enabling selection of a type of contaminant; a contamination modeling diagram, in which a degree of contamination by a contaminant selected from each of the plurality of wells and a two-dimensional or three-dimensional potentiometric surface map of the contaminant based on the degree of contamination by the contaminant are displayed on a contaminated area map; a contamination degree chart indicating a numerical change in the degree of contamination by the contaminant selected from each of the plurality of wells; and a contamination data table indicating the degree of contamination by the selected contaminant on a well basis and on a date basis, wherein the purification period prediction screen comprises a sensor-data-type selection window enabling selection of a type of sensor data, the sensor-data-type selection window being displayed in a contamination map screen, in which a range of a contaminated area, a depth of contamination, a value of each type of sensor data on a well basis, a two-dimensional or three-dimensional potentiometric surface map based on the value of each type of sensor data, a location of the purification device, and locations of the wells are displayed on a contaminated area map, wherein the purification period prediction screen further comprises a period slide bar enabling selection of a start date and an end date, and displays a change history of a selected sensor data during a selected period, the change history of the selected sensor data comprising a range of a contaminated area, a depth of contamination, a value of each type of sensor data on a well basis, and a two-dimensional or three-dimensional potentiometric surface map based on the value of each type of sensor data, wherein the purification period prediction screen is configured to output a predicted value of a degree of contamination after a predetermined period and a predicted value of a purification period, and wherein the predicted value of the degree of contamination after a predetermined period and the predicted value of the purification period are calculated in real-time using a program of a computer executed based on a purification period prediction algorithm comprising an exponential function below:

$$C=C_0e^{-kt}$$

where C indicates a degree of contamination (mg/L) of groundwater after a predetermined period, $C_0$ indicates an initial degree of contamination (mg/L) of groundwater, k indicates a reduction coefficient ($day^{-1}$), and t indicates a time (day), wherein the predicted value of the degree of contamination after a predetermined period is calculated such that the reduction coefficient k ($day^{-1}$) is calculated from the degree of contamination C (mg/L) of groundwater after a predetermined period (day) and the initial degree of contamination $C_0$ (mg/L) of groundwater, among sensor data of the contamination degree sensor, a graph of the exponential function is output, and the predicted value of the degree of contamination after a predetermined period (day) is calculated using the graph, wherein the predicted value of the purification period is calculated such that the reduction coefficient k ($day^{-1}$) is calculated from the degree of contamination C (mg/L) of groundwater after a predetermined period (day) and the initial degree of contamination $C_0$ (mg/L) of groundwater, among sensor data of the contamination degree sensor, a graph of the exponential function is output, a contamination purification target is set using the graph, and a period within which it is required to accomplish the contamination purification target is calculated as the predicted value of the purification period.

2. The IoT-based system according to claim 1, wherein the pumping amount screen comprises:
a pumping amount modeling diagram, in which an amount pumped from each of the plurality of wells, a two-dimensional or three-dimensional potentiometric surface map of a pumping amount based thereon, and a degree of contamination by a contaminant selected from each of the plurality of wells are displayed on a contaminated area map;
a pumping amount chart indicating a change in the amount pumped from each of the plurality of wells; and
a pumping amount data table indicating the pumping amount on a well basis and on a date basis.

3. The IoT-based system according to claim 1, wherein the groundwater level screen comprises:
a groundwater level modeling diagram, in which a groundwater level in each of the plurality of wells, a two-dimensional or three-dimensional potentiometric surface map of the groundwater level based thereon, and a groundwater flow direction diagram are displayed on a contaminated area map;
a strata section diagram indicating the groundwater level displayed on the contaminated area map and a strata in a sectional manner; and
a groundwater level data table indicating the groundwater level on a well basis and on a date basis.

4. The IoT-based system according to claim 1, wherein the indirect purification factor screen comprises:
an indirect purification factor modeling diagram, in which values of indirect purification factors comprising temperature, pH, and rainfall in each of the plurality of wells and a two-dimensional or three-dimensional potentiometric surface map of the indirect purification factors based thereon are displayed on a contaminated area map;
an indirect purification factor chart indicating a change in the values of the indirect purification factors in each of the plurality of wells; and
an indirect purification factor data table indicating the values of the indirect purification factors on a well basis and on a date basis.

5. The IoT-based system according to claim 1, wherein, when each of the plurality of wells in the main screen is clicked and selected, diameters and depths of the wells and specifications of pumps are displayed on a well basis.

6. The IoT-based system according to claim 1, wherein, when each of the plurality of wells in the main screen is clicked and selected, a graph indicating a numerical change in each type of sensor data is displayed.

7. The IoT-based system according to claim 1, wherein, when a peak of a graph displayed in each of a contamination degree chart in the contamination degree screen, the pumping amount chart in the pumping amount screen, and an indirect purification factor chart in the indirect purification factor screen is clicked and selected, a degree of contamination of each contaminant, a pumping amount, and a value of each indirect purification factor on a corresponding date are displayed.

8. The IoT-based system according to claim 1, wherein the distribution history screen comprises a sensor-data-type selection window enabling selection of a type of sensor data, the sensor-data-type selection window being displayed in a contamination map screen, in which a range of a contaminated area, a depth of contamination, a value of each type of sensor data on a well basis, a two-dimensional or three-dimensional potentiometric surface map based on the value of each type of sensor data, a location of the purification device, and locations of the wells are displayed on a contaminated area map, and
wherein the distribution history screen further comprises a period slide bar enabling selection of a start date and an end date, and displays a change history of a selected sensor data during a selected period, the change history of the selected sensor data comprising a range of a contaminated area, a depth of contamination, a value of each type of sensor data on a well basis, and a two-dimensional or three-dimensional potentiometric surface map based on the value of each type of sensor data.

9. The IoT-based system according to claim 1, wherein the distribution comparison screen comprises a sensor-data-type selection window enabling selection of a type of sensor data and a plurality of comparison screens split on a period basis, in each of which a change history of a selected sensor data, which comprises a range of a contaminated area, a depth of contamination, a value of each type of sensor data on a well basis, and a two-dimensional or three-dimensional potentiometric surface map based on the value of each type of sensor data, is displayed on a contaminated area map.

10. The IoT-based system according to claim 1, wherein the purification period prediction screen is configured to enable verification of a contamination reduction state during the selected period based on the change history during the selected period.

11. The IoT-based system according to claim 1, wherein the purification period prediction screen displays an amount of a chemical that is injected and an amount of power that is consumed during a selected period, and calculates and displays a predicted value of an amount of a chemical to be injected and a predicted value of an amount of power to be consumed during a period corresponding to the predicted value of the purification period using a program to which the purification period prediction algorithm is applied based on the amount of the chemical that is injected and the amount of power that is consumed.

12. The IoT-based system according to claim 1, wherein a two-dimensional or three-dimensional potentiometric surface map of the sensor data, a two-dimensional or three-dimensional potentiometric surface map of each contaminant, a two-dimensional or three-dimensional potentiometric surface map of a pumping amount, a two-dimensional or three-dimensional potentiometric surface map of a groundwater level, or a two-dimensional or three-dimensional potentiometric surface map of an indirect purification factor is configured to indicate numerical ranges such that the numerical ranges are distinguished by colors.

13. The IoT-based system according to claim 1, wherein the IoT-based system is configured to allow a purification company or a supervisory institution to have online access thereto so as to perform verification or control.

14. An IoT-based system for measurement of contamination distribution of contaminated groundwater through real-time monitoring of a contamination degree of a contaminated groundwater well for prediction of a purification period based on a measurement result, the IoT-based system comprising:
   a sensor unit mounted in each of a plurality of wells excavated to purify contaminated groundwater, the sensor unit comprising a contamination degree sensor for measuring a degree of contamination by contaminants, a pH sensor, a temperature sensor, a water level sensor, a pumping amount sensor, and a rainfall sensor;
   a server unit configured to collect sensor data transmitted from the sensor unit and to classify the sensor data based on a data type; and
   a web dashboard unit configured to display the sensor data transmitted from the server unit to enable a user to verify or control desired sensor data on a well basis and on a data-type basis in real time, the web dashboard unit comprising a purification-area-based status screen, a main screen, a contamination degree screen, a pumping amount screen, a groundwater level screen, an indirect purification factor screen, a contaminated-area-sensor-data-based movement distribution history screen, a distribution comparison screen, a purification control screen comprising a sensor-data-type selection window enabling selection of a type of sensor data, the sensor-data-type selection window being displayed in a contamination map screen, in which a range of a contaminated area, a depth of contamination, a value of each type of sensor data on a well basis, a two-dimensional or three-dimensional potentiometric surface map based on the value of each type of sensor data, a location of a purification device, locations of the wells, and connection pipes are displayed on a contaminated area map, and a purification period prediction screen displaying a change in the value of each type of sensor data in a contaminated area,
   wherein, when a purification device in the purification control screen is clicked and selected, a purification device operation screen is displayed, and
   wherein the purification device operation screen comprises:
   an entire construction diagram of a purification device in each purification zone;
   a flow indicator indicating a flow of contaminated groundwater through pipes of the purification device, reinjection into the wells, discharge into rainwater, and discharge into sewage; and
   an operation data table indicating a degree of contamination by the contaminants in each well, an amount pumped from each well, a water level in each well, a water level in the purification device, on/off of a pump in each well, on/off of a pump of the purification device, on/off of a pump supplying a chemical, and information about whether the purification device is operating normally,
   wherein the purification device operation screen displays a chart indicating a name of a chemical that is injected, an amount of the chemical that is injected, and a numerical change in the amount of the chemical that is injected,
   wherein on/off of the pump in each well, on/off of the pump of the purification device, and on/off of the pump supplying a chemical are respectively controlled through the purification device operation screen,
   wherein, when an inlet tank and an outlet tank of the purification device displayed in the purification device operation screen are respectively clicked and selected, a graph indicating a numerical change in a degree of contamination by the contaminants is displayed,
   wherein the purification period prediction screen is configured to output a predicted value of a degree of contamination after a predetermined period and a predicted value of a purification period, and wherein the predicted value of the degree of contamination after a predetermined period and the predicted value of the purification period are calculated in real-time using a program of a computer executed based on a purification period prediction algorithm comprising an exponential function below:

$$C = C_0 e^{-kt}$$

where C indicates a degree of contamination (mg/L) of groundwater after a predetermined period, $C_0$ indicates an initial degree of contamination (mg/L) of groundwater, k indicates a reduction coefficient ($day^{-1}$), and t indicates a time (day).

* * * * *